US012603147B2

(12) United States Patent 
Kohl et al.

(10) Patent No.: US 12,603,147 B2 
(45) Date of Patent: Apr. 14, 2026

(54) PREDICTING PROTEIN STRUCTURES USING AUXILIARY FOLDING NETWORKS

(71) Applicant: GDM Holding LLC, Mountain View, CA (US)

(72) Inventors: Simon Kohl, London (GB); Olaf Ronneberger, London (GB); Mikhail Figurnov, London (GB); Alexander Pritzel, London (GB)

(73) Assignee: GDM Holding LLC, Mountain View, CA (US)

( * ) Notice: Subject to any disclaimer, the term of this patent is extended or adjusted under 35 U.S.C. 154(b) by 463 days.

(21) Appl. No.: 18/034,006

(22) PCT Filed: Nov. 23, 2021

(86) PCT No.: PCT/EP2021/082698 
§ 371 (c)(1), 
(2) Date: Apr. 26, 2023

(87) PCT Pub. No.: WO2022/112257 
PCT Pub. Date: Jun. 2, 2022

(65) Prior Publication Data 
US 2023/0395186 A1     Dec. 7, 2023

Related U.S. Application Data

(60) Provisional application No. 63/118,921, filed on Nov. 28, 2020.

(51) Int. Cl. 
*G16B 15/20*          (2019.01) 
*G06N 3/045*          (2023.01) 
(Continued)

(52) U.S. Cl. 
CPC ............. *G16B 15/20* (2019.02); *G06N 3/045* (2023.01); *G06N 3/08* (2013.01); *G16B 40/20* (2019.02)

(58) Field of Classification Search 
CPC ........ G06N 3/045; G06N 3/0499; G06N 3/08; G06N 3/084; G06N 3/09; G16B 15/20; G16B 15/30; G16B 40/20 
See application file for complete search history.

(56) References Cited

U.S. PATENT DOCUMENTS 5,958,784 A      9/1999   Benner 
8,775,341 B1    7/2014   Commons

FOREIGN PATENT DOCUMENTS

CN          109887540 A      6/2019 
CN          110993121 A      4/2020 
(Continued)

OTHER PUBLICATIONS

Office Action in Chinese Appln. No. 202180069629.X, mailed on Jul. 19, 2025, 10 pages (with English translation). 
(Continued)

*Primary Examiner* — Brent Johnston Hoover 
(74) *Attorney, Agent, or Firm* — Fish & Richardson P.C.

(57)          ABSTRACT

Methods, systems, and apparatus, including computer programs encoded on a computer storage medium, for training a structure prediction neural network that comprises an embedding neural network and a main folding neural network. According to one aspect, a method comprises: obtaining a training network input characterizing a training protein; processing the training network input using the embedding neural network and the main folding neural network to generate a main structure prediction; for each auxiliary folding neural network in a set of one or more auxiliary folding neural networks, processing at least a corresponding intermediate output of the embedding neural network to generate an auxiliary structure prediction; determining a gradient of an objective function that includes a respective auxiliary structure loss term for each of the auxiliary folding neural networks; and updating the current 
(Continued)

values of the embedding network parameters and the main folding parameters based on the gradient.

20 Claims, 11 Drawing Sheets

(51) Int. Cl.
   *G06N 3/08*        (2023.01)
   *G16B 40/20*       (2019.01)

(56)                    References Cited

FOREIGN PATENT DOCUMENTS

| | | | | |
|---|---|---|---|---|
| JP | 2008146529 A | 6/2008 | | |
| WO | WO 2020/058174 | 3/2020 | | |
| WO | WO-2020058174 A1 * | 3/2020 | ............. | G16B 15/20 |
| WO | WO-2020058177 A1 * | 3/2020 | ............. | G16B 40/20 |

OTHER PUBLICATIONS

Office Action in European Appln. No. 21816056.2, Jul. 21, 2025, 6 pages.

[No Author Listed] "UniProt: the universal protein knowledgebase in 2021," Nucleic Acids Res., Nov. 25, 2020, 49:D480-D489.

[No Author Listed], "Protein Data Bank: the single global archive for 3D macromolecular structure data," Nucleic Acids Res., Jan. 8, 2019, 47(D1):D520-D528.

Abadi et al., "TensorFlow: large-scale machine learning on heterogeneous systems," CoRR, Mar. 14, 2016, arxiv.org/abs/1603.04467, 19 pages.

Abriata et al., "A further leap of improvement in tertiary structure prediction in CASP13 prompts new routes for future assessments," Proteins, Jul. 25, 2019, 87(12):1100-1112.

Alley et al., "Unified rational protein engineering with sequence-based deep representation learning," Nat. Methods, Oct. 21, 2019, 16(12):1315-1322.

AlQuraishi et al., "End-to-end differentiable learning of protein structure," Cell Syst., Apr. 24, 2019, 8:292-301.

Altschuh et al., "Correlation of coordinated amino acid substitutions with function in viruses related to tobacco mosaic virus," J. Mol. Biol., Feb. 20, 1987, 193(4):693-707.

Anfinsen, "Principles that govern the folding of protein chains," Science, Jul. 20, 1973, 181:223-230.

Ashish et al., "TensorFlow: large-scale machine learning on heterogeneous systems," CoRR, Mar. 14, 2016, arxiv.org/abs/1603. 04467, 19 pages.

Bai et al., "How cryo-EM is revolutionizing structural biology," Trends Biochem. Sci., Nov. 7, 2014, 40:49-57.

Bisong et al., "Building Machine Learning and Deep Learning Models on Google Cloud Platform," A Comprehensive Guide for Beginners, 2019, pp. 59-64.

Brini et al., "Protein storytelling through physics," Science, Nov. 27, 2020, 370(6520):23 pages.

Carreira et al., "Human pose estimation with iterative error feedback," Proc. IEEE Conference on Computer Vision and Pattern Recognition, 2016, pp. 4733-4742.

Debruycker et al., "An embedded lipid in the multidrug transporter LmrP suggests a mechanism for polyspecificity," Nat. Struct. Mol. Biol., 2020, 27:829-835.

Deepmind.google [online], "Open sourcing Sonnet—a new library for constructing neural networks," Apr. 7, 2017, retrieved on Nov. 7, 2023, retrieved from URL<https://deepmind.google/discover/blog/open-sourcing-sonnet-a-new-library-for-constructing-neural-networks/>, 4 pages.

Defay et al., "Evaluation of Current Techniques for Ab Initio Protein Structure Prediction," Proteins: Structure, Function, and Genetics, 1995, 23:431-445.

Deorowicz et al., "FAMSA: fast and accurate multiple sequence alignment of huge protein families," Sci. Rep., Sep. 27, 2016, 6(33964):1-13.

Devlin et al., "BERT: pre-training of deep bidirectional transformers for language understanding," Proc. 2019 Conference of the North American Chapter of the Association for Computational Linguistics: Human Language Technologies, Jun. 2-7, 2019, 1:4171-4186.

Dill et al., "The protein folding problem," Annu. Rev. Biophys., 2008, 37:289-316.

Drobysheva et al., "Structure and function of virion RNA polymerase of a crAss-like phage," Nature, Jan. 2021, 589(7841):306-309.

Dunne et al., "The M23 peptidase domain of the *Staphylococcal* phage 2638A endolysin," PDB, Sep. 7, 2020, 12 pages.

Eastman et al., "OpenMM 7: rapid development of high performance algorithms for molecular dynamics," PLOS Comput. Biol., Jul. 26, 2017, 13(7):e1005659.

Eddy, "Accelerated profile HMM searches," PLOS Comput. Biol., Oct. 20, 2011, 7(10):e1002195.

ElGamacy et al., "An interface-driven design strategy yields a novel, corrugated protein architecture," ACS Synth. Biol., Aug. 27, 2018, 7(9):72226-2235.

Fariselli et al., "Prediction of contact maps with neural networks and correlated mutations," Protein Eng., Nov. 2001, 14:835-843.

Flaugnatti et al., "Structural basis for loading and inhibition of a bacterial T6SS phospholipase effector by the VgrG spike," EMBO J. 39, 2020, 39:e104129.

Flower et al., "Structure of SARS-CoV-2 ORF8, a rapidly evolving immune evasion protein," Proc. Natl Acad. Sci., Nov. 12, 2020, 118:e2021785118.

Gupta et al., "CryoEM and AI reveal a structure of SARS-CoV-2 Nsp2, a multifunctional protein involved in key host processes," Res Sq., May 19, 2021, 46 pages.

Harris et al., "Array programming with NumPy," Nature, 2020, 585(7825)357-362.

He et al., "Deep residual learning for image recognition," Proc. IEEE Conference on Computer Vision and Pattern Recognition, 2016, pp. 770-778.

Heinzinger et al., "Modeling aspects of the language of life through transfer-learning protein sequences," BMC Bioinformatics, Dec. 17, 2019, 20:723.

Hornak et al., "Comparison of multiple Amber force fields and development of improved protein backbone parameters," Proteins, Nov. 15, 2006, 65(3):712-725.

Huang et al., "CCNet: criss-cross attention for semantic segmentation," Proc. IEEE/CVF International Conference on Computer Vision, 2019, pp. 603-612.

Ingraham et al., "Generative models for graph-based protein design," Advances in Neural Information Processing Systems 32, 2019, 10 pages.

Ingraham et al., "Learning protein structure with a differentiable simulator," Proc. International Conference on Learning Representations, Dec. 20, 2018, 24 pages.

International Preliminary Report on Patentability International Appln. No. PCT/EP2021/082698, dated Jun. 8, 2023, 13 pages.

International Search Report and Written Opinion in International Appln. No. PCT/EP2021/082698, dated Mar. 1, 2022, 22 pages.

Jaskolski et al., "A brief history of macromolecular crystallography, illustrated by a family tree and its Nobel fruits," FEBS J., Apr. 3, 2014, 281(18):3985-4009.

Jiang et al., "MrpH, a new class of metal-binding adhesin, requires zinc to mediate biofilm formation," PLoS Pathogens, Aug. 11, 2020, 16:e1008707.

Johnson et al., "Hidden Markov model speed heuristic and iterative HMM search procedure," BMC Bioinformatics, Aug. 18, 2010, 11:431.

Jones et al., "PSICOV: precise structural contact prediction using sparse inverse covariance estimation on large multiple sequence alignments," Bioinformatics, Jan. 2012, 28(2):184-190.

Jumper et al., "Highly accurate protein structure prediction with Alphafold—Supplementary Information," Nature, Jul. 15, 2021, 596(7873):583-589.

(56)                    References Cited

OTHER PUBLICATIONS

Jumper et al., "Highly accurate protein structure prediction with Alphafold," Nature, Jul. 15, 2021, 596(7873):583-589.

Knighton et al., "Crystal Structure of the Catalytic Subunit of Cyclic Adenosine Monophosphate-Dependent Protein Kinase," Science, Jul. 1991, 253:5018:407-414.

Kryshtafovych et al., "Critical assessment of methods of protein structure prediction (CASP)-round XIII," Proteins, Oct. 7, 2019, 87(12):1011-1020.

Kuhlman et al., "Advances in protein structure prediction and design," Nat. Rev. Mol. Cell Biol., Aug. 15, 2019, 20(11):681-697.

Lei Ba et al., "Layer Normalization," CoRR, Jul. 21, 2016, arXiv:1607. 06450, 14 pages.

Li et al., "Deducing high-accuracy protein contact-maps from a triplet of coevolutionary matrices through deep residual convolutional networks," PLOS Comput. Biol., Mar. 26, 2021, 17(3):e1008865.

Li et al., "Universal transforming geometric network," CoRR, Aug. 2, 2019, arxiv.org/abs/1908.00723, 11 pages.

Lim et al., "The structure of human CST reveals a decameric assembly bound to telomeric DNA," Science, Jun. 5, 2020, 368(6495):1081-1085.

Mariani et al., "IDDT: a local superposition-free score for comparing protein structures and models using distance difference tests," Bioinformatics, Nov. 1, 2013; 29(21) 2722-2728.

Marks et al., "Protein 3D structure computed from evolutionary sequence variation," PLoS One, Dec. 7, 2011, 6(12):e28766.

Marks et al., "Protein structure prediction from sequence variation," Nat. Biotechnol., Nov. 2012, 30(11):1072-1080.

Mirabello et al., "rawMSA: end-to-end deep learning using raw multiple sequence alignments," PLoS One, Aug. 15, 2019, 14(8):e0220182.

Mirdita et al., "Uniclust databases of clustered and deeply annotated protein sequences and alignments," Nucleic Acids Res., Nov. 29, 2016, 45(D1):D170-D176.

Mitchell et al., "MGnify: the microbiome analysis resource in 2020," Nucleic Acids Res., Jan. 2020, 48(D1):D570-D578.

Pearce et al., "Deep learning techniques have significantly impacted protein structure prediction and protein design," Curr. Opin. Struct. Biol., Jun. 2021, 68:194-207.

Pereira et al., "High-accuracy protein structure prediction in CASP14," Proteins, Jul. 3, 2021, 89(12):1687-1699.

Prodromou et al., "Identification and Structural Characterization of the ATP/ADP-Binding Site in the Hsp90 Molecular Chaperone," Cell, Jul. 11, 1991, 90:65-75.

Qian et al., "Predicting the secondary structure of globular proteins using neural network models," J. Mol. Biol., Aug. 20, 1988, 202(2):865-884.

Rao et al., "MSA transformer," Proceedings of the 38th International Conference on Machine Learning, PMLR, 2021, 139:8844-8856.

Remmert et al., "HHblits: lightning-fast iterative protein sequence searching by HMM-HMM alignment," Nat. Methods, Feb. 2012, 9(2):173-175.

Rives et al., "Biological structure and function emerge from scaling unsupervised learning to 250 million protein sequences," Proc. Natl Acad. Sci., Apr. 5, 2021, 118(15):e2016239118.

Rossum et al., "Python 3 Reference Manual," PythonLabs, Apr. 10, 2002, 79 pages.

Roy et al., "I-TASSER: a unified platform for automated protein structure and function prediction," Nat. Protocols, Apr. 2010, 5(4):725-738.

Šali et al., "Comparative protein modelling by satisfaction of spatial restraints," J. Mol. Biol., Dec. 5, 1993, 234:779-815.

Senior et al., "Improved protein structure prediction using potentials from deep learning," Nature, 2020, 577:706-710.

Senior et al., "Protein structure prediction using multiple deep neural networks in the 13th Critical Assessment of Protein Structure Prediction (CASP13)," Proteins, Oct. 10, 2019, 87(12):1141-1148.

Shindyalov et al., "Can three-dimensional contacts in protein structures be predicted by analysis of correlated mutations?," Protein Eng., Mar. 1, 1994, 7(3):349-358.

Sippl, "Calculation of conformational ensembles from potentials of mean force: An approach to the knowledge-based prediction of local structures in globular proteins," J. Mol. Biol., Jun. 20, 1990, 213:859-883.

Steinegger et al., "Clustering huge protein sequence sets in linear time," Nat. Commun., Jun. 29, 2018, 9(1):2542.

Steinegger et al., "MMseqs2 enables sensitive protein sequence searching for the analysis of massive data sets," Nat. Biotechnol., 2017, 35:1026-1028.

Steinegger et al., "Protein-level assembly increases protein sequence recovery from metagenomic samples manyfold," Nat. Methods, Nov. 27, 2018, 16:603-606.

Steinegger et al., "HH-suite3 for fast remote homology detection and deep protein annotation," BMC Bioinformatics, Sep. 14, 2019, 20(473):15 pages.

Suzek et al., "UniRef clusters: a comprehensive and scalable alternative for improving sequence similarity searches," Bioinformatics, Mar. 2015, 31(6):926-932.

tensorflow.org [online], "XLA: Optimizing Compiler for Machine Learning," Nov. 2018, retrieved on Nov. 7, 2023, retrieved from URL<https://www.tensorflow.org/xla/>, 8 pages.

Thompson, "Advances in methods for atomic resolution macromolecular structure determination," F1000Res. 9, Jul. 2, 2020, 9(FacultyRev):667.

Thornton et al., "Prediction of Progress at Least," Nature, Nov. 1991, 354:105-106.

Tu et al., "Auto-context and its application to high-level vision tasks and 3D brain image segmentation," IEEE Trans. Pattern Anal, Mach. Intell., Oct. 2010, 32(10):1744-1757.

Tunyasuvunakool et al., "Highly accurate protein structure prediction for the human proteome," Nature, Jul. 22, 2021, 21 pages.

Vaswani et al., "Attention is all you need," Advances in Neural Information Processing Systems 30, 2017, pp. 5998-6008.

Wang et al., "Accurate de novo prediction of protein contact map by ultra-deep learning model," PLOS Comput. Biol., Jan. 5, 2017, 13(10):e1005324.

Wang et al., "Axial-deeplab: stand-alone axial-attention for panoptic segmentation," European Conference on Computer Vision, Oct. 29, 2020, pp. 108-126.

Weigt et al., "Identification of direct residue contacts in protein-protein interaction by message passing," Proc. Natl Acad. Sci., Jan. 6, 2009, 106(1):67-72.

Wu et al., "Analysis of several key factors influencing deep learning-based inter-residue contact prediction," Bioinformatics, Feb. 2020, 36(4):1091-1098.

Wüthrich, "The way to NMR structures of proteins," Nat. Struct. Biol., Nov. 2001, 8:923-925.

Xie et al., "Self-training with noisy student improves imagenet classification," Proceedings of the IEEE/CVF Conference on Computer Vision and Pattern Recognition (CVPR), 2020, pp. 10687-10698.

Xu et al., "Improved protein structure prediction by deep learning irrespective of co-evolution information," Nat. Mach. Intell., Jul. 2021, 3:601-609.

Yang et al., "Improved protein structure prediction using predicted interresidue orientations," Proc. Natl Acad. Sci., Jan. 2, 2020, 117(3):1496-1503.

Zemla, "LGA: a method for finding 3D similarities in protein structures," Nucleic Acids Res., Jul. 1, 2003, 31(13):3370-3374.

Zhang et al., "Scoring function for automated assessment of protein structure template quality," Proteins, Oct. 8, 2004, 57(4):702-710.

Zheng et al., "Deep-learning contact-map guided protein structure prediction in CASP13," Proteins, Jul. 31, 2019, 87(12):1149-1164.

Baldi et al., "A machine learning strategy for protein analysis," IEEE Intelligent Systems, Mar.-Apr. 2002, 17.2:28-35.

Bohr et al., "Protein secondary structure and homology by neural networks The α-helices in rhodopsin," FEBS Lett., Dec. 1988, 241(1-2):223-228.

(56)          References Cited

OTHER PUBLICATIONS

Golkov et al., "Protein contact prediction from amino acid co-evolution using convolutional networks for graph-valued images," Advances in Neural Information Processing Systems 29 (NIPS 2016), 2016, 9 pages.

Hochreiter et al., "Fast model-based protein homology detection without alignment," Bioinformatics, May 11, 2007, 23(14):1728-1736.

Lena et al., "Deep Architectures for Protein Contact Map Prediction," Bioinformatics, Oct. 2012, 28(19):2449-2457.

Notice of Allowance in Chinese Appln. No. 202180069629.X, mailed on Jan. 8, 2026, 5 pages (with English translation).

* cited by examiner

PROTEIN STRUCTURE PREDICTION SYSTEM
100

EMBEDDING NEURAL NETWORK 200

EMBEDDING NEURAL NETWORK UPDATE BLOCK

MSA UPDATE BLOCK 400

PAIR UPDATE BLOCK 500

FOLDING NEURAL NETWORK 600

900

OBTAIN TRAINING INPUT CHARACTERIZING A PROTEIN — 902

OBTAIN TARGET STRUCTURE FOR THE PROTEIN — 904

PROCESS TRAINING INPUT USING THE EMBEDDING NEURAL NETWORK AND THE MAIN FOLDING NEURAL NETWORK — 906

PROCESS INPUTS FROM EMBEDDING NEURAL NETWORK USING EACH OF ONE OR MORE AUXILIARY FOLDING NEURAL NETWORKS — 908

DETERMINE UPDATES TO PARAMETER VALUES — 910

**GENERATING A MSA REPRESENTATION FOR
AN AMINO ACID CHAIN IN THE PROTEIN**

GENERATING INITIAL PAIR EMBEDDINGS

PREDICTING PROTEIN STRUCTURES USING AUXILIARY FOLDING NETWORKS

CROSS-REFERENCE TO RELATED APPLICATIONS

This application is a National Stage Application under 35 U.S.C. § 371 and claims the benefit of International Application No. PCT/EP2021/082698, filed Nov. 23, 2021, which claims the benefit of the filing date of U.S. Provisional Patent Application Ser. No. 63/118,921, which was filed on Nov. 28, 2020, and which is incorporated herein by reference in its entirety.

BACKGROUND

This specification relates to predicting protein structures.

A protein is specified by one or more sequences ("chains") of amino acids. An amino acid is an organic compound which includes an amino functional group and a carboxyl functional group, as well as a side chain (i.e., group of atoms) that is specific to the amino acid. Protein folding refers to a physical process by which one or more sequences of amino acids fold into a three-dimensional (3-D) configuration. The structure of a protein defines the 3-D configuration of the atoms in the amino acid sequences of the protein after the protein undergoes protein folding. When in a sequence linked by peptide bonds, the amino acids may be referred to as amino acid residues.

Predictions can be made using machine learning models. Machine learning models receive an input and generate an output, e.g., a predicted output, based on the received input. Some machine learning models are parametric models and generate the output based on the received input and on values of the parameters of the model. Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification describes a neural network system implemented as computer programs on one or more computers in one or more locations for predicting protein structures.

As used throughout this specification, the term "protein" can be understood to refer to any biological molecule that is specified by one or more sequences (or "chains") of amino acids. For example, the term protein can refer to a protein domain, e.g., a portion of an amino acid chain of a protein that can undergo protein folding nearly independently of the rest of the protein. As another example, the term protein can refer to a protein complex, i.e., that includes multiple amino acid chains that jointly fold into a protein structure.

A "multiple sequence alignment" (MSA) for an amino acid chain in a protein specifies a sequence alignment of the amino acid chain with multiple additional amino acid chains, e.g., from other proteins, e.g., homologous proteins. More specifically, the MSA can define a correspondence between the positions in the amino acid chain and corresponding positions in multiple additional amino acid chains. A MSA for an amino acid chain can be generated, e.g., by processing a database of amino acid chains using any appropriate computational sequence alignment technique, e.g., progressive alignment construction. The amino acid chains in the MSA can be understood as having an evolutionary relationship, e.g., where each amino acid chain in the MSA may share a common ancestor. The correlations between the amino acids in the amino acid chains in a MSA for an amino acid chain can encode information that is relevant to predicting the structure of the amino acid chain.

An "embedding" of an entity (e.g., a pair of amino acids) can refer to a representation of the entity as an ordered collection of numerical values, e.g., a vector or matrix of numerical values.

The structure of a protein can be defined by a set of structure parameters. A set of structure parameters defining the structure of a protein can be represented as an ordered collection of numerical values. A few examples of possible structure parameters for defining the structure of a protein are described in more detail next.

In one example, the structure parameters defining the structure of a protein include: (i) location parameters, and (ii) rotation parameters, for each amino acid in the protein.

The location parameters for an amino acid can specify a predicted 3-D spatial location of a specified atom in the amino acid in the structure of the protein. The specified atom can be the alpha carbon atom in the amino acid, i.e., the carbon atom in the amino acid to which the amino functional group, the carboxyl functional group, and the side chain are bonded. As another example, the specified atom can be the beta carbon atom in the amino acid. The location parameters for an amino acid can be represented in any appropriate coordinate system, e.g., a three-dimensional [x, y, z] Cartesian coordinate system.

The rotation parameters for an amino acid can specify the predicted "orientation" of the amino acid in the structure of the protein. More specifically, the rotation parameters can specify a 3-D spatial rotation operation that, if applied to the coordinate system of the location parameters, causes the three "main chain" atoms in the amino acid to assume fixed positions relative to the rotated coordinate system. The three main chain atoms in the amino acid can refer to the linked series of nitrogen, alpha carbon, and carbonyl carbon atoms in the amino acid. The rotation parameters for an amino acid can be represented, e.g., as an orthonormal 3×3 matrix with determinant equal to 1.

Generally, the location and rotation parameters for an amino acid define an egocentric reference frame for the amino acid. In this reference frame, the side chain for each amino acid may start at the origin, and the first bond along the side chain (i.e., the alpha carbon-beta carbon bond) may be along a defined direction.

In another example, the structure parameters defining the structure of a protein can include a "distance map" that characterizes a respective estimated distance (e.g., measured in angstroms) between each pair of amino acids in the protein. A distance map can characterize the estimated distance between a pair of amino acids, e.g., by a probability distribution over a set of possible distances between the pair of amino acids.

In another example, the structure parameters defining the structure of a protein can define a three-dimensional (3D) spatial location of each atom in each amino acid in the structure of the protein.

The protein structure prediction system described herein can be used to obtain a ligand such as a drug or a ligand of an industrial enzyme. For example, a method of obtaining a ligand may include obtaining a target amino acid sequence, in particular the amino acid sequence of a target protein, e.g. a drug target, and processing an input based on the target amino acid sequence using the protein structure prediction system to determine a (tertiary) structure of the target protein, i.e., the predicted protein structure. The method may then include evaluating an interaction of one or more candidate ligands with the structure of the target protein. The method may further include selecting one or more of the candidate ligands as the ligand dependent on a result of the evaluating of the interaction.

In some implementations, evaluating the interaction may include evaluating binding of the candidate ligand with the structure of the target protein. For example, evaluating the interaction may include identifying a ligand that binds with sufficient affinity for a biological effect. In some other implementations, evaluating the interaction may include evaluating an association of the candidate ligand with the structure of the target protein which has an effect on a function of the target protein, e.g., an enzyme. The evaluating may include evaluating an affinity between the candidate ligand and the structure of the target protein, or evaluating a selectivity of the interaction. The candidate ligand(s) may be selected according to which have the highest affinity.

The candidate ligand(s) may be derived from a database of candidate ligands, and/or may be derived by modifying ligands in a database of candidate ligands, e.g., by modifying a structure or amino acid sequence of a candidate ligand, and/or may be derived by stepwise or iterative assembly/optimization of a candidate ligand.

The evaluation of the interaction of a candidate ligand with the structure of the target protein may be performed using a computer-aided approach in which graphical models of the candidate ligand and target protein structure are displayed for user-manipulation, and/or the evaluation may be performed partially or completely automatically, for example using standard molecular (protein-ligand) docking software. In some implementations the evaluation may include determining an interaction score for the candidate ligand, where the interaction score includes a measure of an interaction between the candidate ligand and the target protein. The interaction score may be dependent upon a strength and/or specificity of the interaction, e.g., a score dependent on binding free energy. A candidate ligand may be selected dependent upon its score, e.g. as the candidate ligand having the highest interaction score.

In some implementations the target protein includes a receptor or enzyme and the ligand is an agonist or antagonist of the receptor or enzyme. In some implementations the method may be used to identify the structure of a cell surface marker. This may then be used to identify a ligand, e.g., an antibody or a label such as a fluorescent label, which binds to the cell surface marker. This may be used to identify and/or treat cancerous cells.

In some implementations the ligand is a drug and the predicted structure of each of a plurality of target proteins is determined, and the interaction of the one or more candidate ligands with the predicted structure of each of the target proteins is evaluated. Then one or more of the candidate ligands may be selected either to obtain a ligand that (functionally) interacts with each of the target proteins, or to obtain a ligand that (functionally) interacts with only one of the target proteins. For example in some implementations it may be desirable to obtain a drug that is effective against multiple drug targets. Also or instead it may be desirable to screen a drug for off-target effects. For example in agriculture it can be useful to determine that a drug designed for use with one plant species does not interact with another, different plant species and/or an animal species.

In some implementations the candidate ligand(s) may include small molecule ligands, e.g., organic compounds with a molecular weight of <900 daltons. In some other implementations the candidate ligand(s) may include polypeptide ligands, i.e., defined by an amino acid sequence.

In some cases, the protein structure prediction system can be used to determine the structure of a candidate polypeptide ligand, e.g., a drug or a ligand of an industrial enzyme. The interaction of this with a target protein structure may then be evaluated; the target protein structure may have been determined using a structure prediction neural network or using conventional physical investigation techniques such as x-ray crystallography and/or magnetic resonance techniques and/or cryogenic electron microscopy.

In another aspect there is provided a method of using a protein structure prediction system to obtain a polypeptide ligand (e.g., the molecule or its sequence). The method may include obtaining an amino acid sequence of one or more candidate polypeptide ligands. The method may further include using the protein structure prediction system to determine (tertiary) structures of the candidate polypeptide ligands. The method may further include obtaining a target protein structure of a target protein, in silico and/or by physical investigation, and evaluating an interaction between the structure of each of the one or more candidate polypeptide ligands and the target protein structure. The method may further include selecting one or more of the candidate polypeptide ligands as the polypeptide ligand dependent on a result of the evaluation.

As before evaluating the interaction may include evaluating binding of the candidate polypeptide ligand with the structure of the target protein, e.g., identifying a ligand that binds with sufficient affinity for a biological effect, and/or evaluating an association of the candidate polypeptide ligand with the structure of the target protein which has an effect on a function of the target protein, e.g., an enzyme, and/or evaluating an affinity between the candidate polypeptide ligand and the structure of the target protein, or evaluating a selectivity of the interaction. In some implementations the polypeptide ligand may be an aptamer. Again the polypeptide candidate ligand(s) may be selected according to which have the highest affinity.

As before the selected polypeptide ligand may comprise a receptor or enzyme and the ligand may be an agonist or antagonist of the receptor or enzyme. In some implementations the polypeptide ligand may comprise an antibody and the target protein may comprise an antibody target, for example a virus, in particular a virus coat protein, or a protein expressed on a cancer cell. In these implementations the antibody binds to the antibody target to provide a therapeutic effect. For example, the antibody may bind to the target and act as an agonist for a particular receptor; alternatively, the antibody may prevent binding of another ligand to the target, and hence prevent activation of a relevant biological pathway.

Implementations of the method may further include synthesizing, i.e., making, the small molecule or polypeptide ligand. The ligand may be synthesized by any conventional chemical techniques and/or may already be available, e.g., may be from a compound library or may have been synthesized using combinatorial chemistry.

The method may further include testing the ligand for biological activity in vitro and/or in vivo. For example the ligand may be tested for ADME (absorption, distribution, metabolism, excretion) and/or toxicological properties, to screen out unsuitable ligands. The testing may include, e.g., bringing the candidate small molecule or polypeptide ligand into contact with the target protein and measuring a change in expression or activity of the protein.

In some implementations a candidate (polypeptide) ligand may include: an isolated antibody, a fragment of an isolated antibody, a single variable domain antibody, a bi- or multi-specific antibody, a multivalent antibody, a dual variable domain antibody, an immuno-conjugate, a fibronectin molecule, an adnectin, an DARPin, an avimer, an affibody, an anticalin, an affilin, a protein epitope mimetic or combinations thereof. A candidate (polypeptide) ligand may include an antibody with a mutated or chemically modified amino acid Fc region, e.g., which prevents or decreases ADCC (antibody-dependent cellular cytotoxicity) activity and/or increases half-life when compared with a wild type Fc region. Candidate (polypeptide) ligands may include antibodies with different CDRs (Complementarity-Determining Regions).

The protein structure prediction system described herein can also be used to obtain a diagnostic antibody marker of a disease. There is also provided a method that, for each of one or more candidate antibodies e.g. as described above, uses the protein structure prediction system to determine a predicted structure of the candidate antibody. The method may also involve obtaining a target protein structure of a target protein, evaluating an interaction between the predicted structure of each of the one or more candidate antibodies and the target protein structure, and selecting one of the one or more of the candidate antibodies as the diagnostic antibody marker dependent on a result of the evaluating, e.g. selecting one or more candidate antibodies that have the highest affinity to the target protein structure. The method may include making the diagnostic antibody marker. The diagnostic antibody marker may be used to diagnose a disease by detecting whether it binds to the target protein in a sample obtained from a patient, e.g. a sample of bodily fluid. As described above, a corresponding technique can be used to obtain a therapeutic antibody (polypeptide ligand).

Misfolded proteins are associated with a number of diseases. Thus in a further aspect there is provided a method of using the protein structure prediction system to identify the presence of a protein mis-folding disease. The method may include obtaining an amino acid sequence of a protein and using the protein structure prediction system to determine a structure of the protein. The method may further include obtaining a structure of a version of the protein obtained from a human or animal body, e.g., by conventional (physical) methods. The method may then include comparing the structure of the protein with the structure of the version obtained from the body and identifying the presence of a protein mis-folding disease dependent upon a result of the comparison. That is, mis-folding of the version of the protein from the body may be determined by comparison with the in silico determined structure.

In general identifying the presence of a protein mis-folding disease may involve obtaining an amino acid sequence of a protein, using an amino acid sequence of the protein to determine a structure of the protein, as described herein, and comparing the structure of the protein with the structure of a baseline version of the protein, identifying the presence of a protein mis-folding disease dependent upon a result of the comparison. For example the compared structures may be those of a mutant and wild-type protein. In implementations the wild-type protein may be used as the baseline version but in principle either may be used as the baseline version.

In some other aspects a computer-implemented method as described above or herein may be used to identify active/binding/blocking sites on a target protein from its amino acid sequence.

According to one aspect there is provided a method of training a structure prediction neural network, wherein the structure prediction neural network comprises (i) an embedding neural network having a plurality of embedding parameters and that is configured to receive a network input characterizing a protein and to process the network input in accordance with the embedding parameters to generate an embedding output for the network input and (ii) a main folding neural network having a plurality of main folding parameters and that is configured to receive the embedding output and to process the main folding input in accordance with the main folding parameters to generate a main structure prediction that defines a predicted structure of the protein, the method comprising: obtaining a training network input characterizing a training protein and data specifying a target protein structure for the training protein; processing the training network input using the embedding neural network and in accordance with current values of the embedding parameters to generate a training embedding output for the training network input; processing the training embedding output using the main folding neural network and in accordance with current values of the main folding parameters to generate a main structure prediction that defines a main predicted structure of the training protein; for each auxiliary folding neural network in a set of one or more auxiliary folding neural networks that each have a respective plurality of auxiliary folding parameters, processing at least a corresponding intermediate output of the embedding neural network using the auxiliary folding neural network and in accordance with the current values of the respective auxiliary folding parameters of the auxiliary folding neural network to generate an auxiliary structure prediction that defines an auxiliary predicted structure of the training protein; determining a gradient of an objective function that includes: a main structure loss term that characterizes a similarity between: (i) the main predicted structure defined by the main structure prediction, and (ii) the target protein structure for the training protein; and a respective auxiliary structure loss term for each of the auxiliary folding neural networks that characterizes a similarity between: (i) the auxiliary predicted structure defined by the auxiliary structure prediction generated by the auxiliary structure prediction neural network, and (ii) the target protein structure for the training protein; and updating the current values of the embedding network parameters, the main folding parameters, and the respective auxiliary folding parameters of the one or more auxiliary folding neural networks based on the gradient.

In some implementations, each auxiliary folding neural network has a same neural network architecture as the main folding neural network.

In some implementations, the set of one or more auxiliary folding neural networks comprises a plurality of auxiliary folding neural networks and the objective function constrains the auxiliary folding neural networks to share parameter values.

In some implementations, the objective function constrains the auxiliary folding neural networks and the main folding neural network to share parameter values.

In some implementations, the network input comprises a respective initial pair embedding for each pair of amino acids in the protein, the embedding neural network comprises a sequence of update blocks, and each update block performs operations comprising: receiving a block input comprising a respective current pair embedding for each pair of amino acids in the protein; and updating the respective current pair embeddings for each pair of amino acids in the protein to generate a respective updated pair embedding for each pair of amino acids in the protein, and the embedding output comprises at least the updated pair embeddings generated by a last update block in the sequence.

In some implementations, each auxiliary folding neural network corresponds to a different one of the update blocks in the sequence that is not the last update block in the sequence, and each auxiliary folding neural network is configured to receive as input at least the updated pair embeddings generated by the corresponding update block.

In some implementations, the network input further comprises an initial multiple sequence alignment (MSA) embedding that represents a respective multiple sequence alignment corresponding to each chain in the protein, the block input to each of the update blocks further comprises a current MSA embedding; and the operations performed by each update block further comprise: updating the current MSA embedding to generate an updated MSA embedding.

In some implementations, the input for each auxiliary folding neural network further comprises the updated MSA embedding generated by the corresponding update block.

In some implementations, each auxiliary folding neural network is configured to: generate, from the auxiliary structure prediction generated by the auxiliary folding neural network, a transformed structure prediction that has a same dimensionality as the updated pair embeddings; combine the transformed structure prediction with the updated pair embeddings to generate further updated pair embeddings; and provide the further updated pair embeddings as input to an update block that follows the current update block in the sequence.

In some implementations, the auxiliary folding prediction comprises structure parameters that specify, for each amino acid, a predicted 3-D spatial location of a specified atom in the amino acid in the structure of the protein; and generating the transformed structure prediction comprises: generating, from the predicted 3-D spatial locations for the amino acids specified by the structure parameters, a distance map that characterizes, for each pair of amino acids in the protein, a respective estimated distance between the pair of amino acids in the structure of the protein; and generating, from the distance map, a transformed distance map that has a same dimensionality as the updated pair embeddings.

In some implementations, the auxiliary folding prediction comprise structure parameters that specify a distance map that characterizes, for each pair of amino acids in the protein, a respective estimated distance between the pair of amino acids in the structure of the protein; and generating the transformed structure prediction comprises: generating, from the distance map specified by the structure parameters, a transformed distance map that has a same dimensionality as the initial pair embeddings.

In some implementations, the method further comprises, after the training, obtaining a new network input characterizing a new protein; and processing the new network input using the trained structure prediction neural network to generate a new main structure prediction that defines a predicted structure of the new protein.

Particular embodiments of the subject matter described in this specification can be implemented so as to realize one or more of the following advantages.

The system described in this specification predicts the structure of a protein using a neural network that, at least during training, includes one or more auxiliary folding neural networks in addition to a main folding neural network that generates the actual predicted output that predicts the structure of the protein and an embedding neural network that generates the input to the main folding neural network. Each auxiliary folding neural network corresponds to and receives inputs from one of multiple update blocks within the embedding neural network. Including the auxiliary folding neural networks as part of the neural network during training allows the embedding neural network to receive richer training signals and therefore learn to generate higher quality embeddings, e.g., relative to only learning based on errors in predictions made by the main folding neural network and optionally on errors in outputs for one or more auxiliary tasks, resulting in higher quality predictions being generated by the main folding neural network once the neural network has been trained.

In some cases, the auxiliary neural networks are also included in the neural network after training, and each auxiliary neural network uses the auxiliary structure prediction that the neural network generates to modify the output of the corresponding update block. This can further improve the quality of the generated embeddings that are provided as input to the main folding neural network, further improving the quality of the predictions generated by the main folding neural network after training.

The system described in this specification can predict the structure of a protein by a single forward pass through a collection of jointly trained neural networks, which may take less than one second. In contrast, some conventional systems predict the structure of a protein by an extended search process through the space of possible protein structures to optimize a scalar score function, e.g., using simulated annealing or gradient descent techniques. Such a search process may require millions of search iterations and consume hundreds of central processing unit (CPU) hours. Predicting protein structures by a single forward pass through a collection of neural networks may enable the system described in this specification to consume fewer computational resources (e.g., memory and computing power) than systems that predict protein structures by an iterative search process.

The structure of a protein determines the biological function of the protein. Therefore, determining protein structures may facilitate understanding life processes (e.g., including the mechanisms of many diseases) and designing proteins (e.g., as drugs, or as enzymes for industrial processes). For example, which molecules (e.g., drugs) will bind to a protein (and where the binding will occur) depends on the structure of the protein. Since the effectiveness of drugs can be influenced by the degree to which they bind to proteins (e.g., in the blood), determining the structures of different proteins may be an important aspect of drug development. However, determining protein structures using physical experiments (e.g., by x-ray crystallography) can be time-consuming and very expensive. Therefore, the protein prediction system described in this specification may facilitate areas of biochemical research and engineering which involve proteins (e.g., drug development).

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
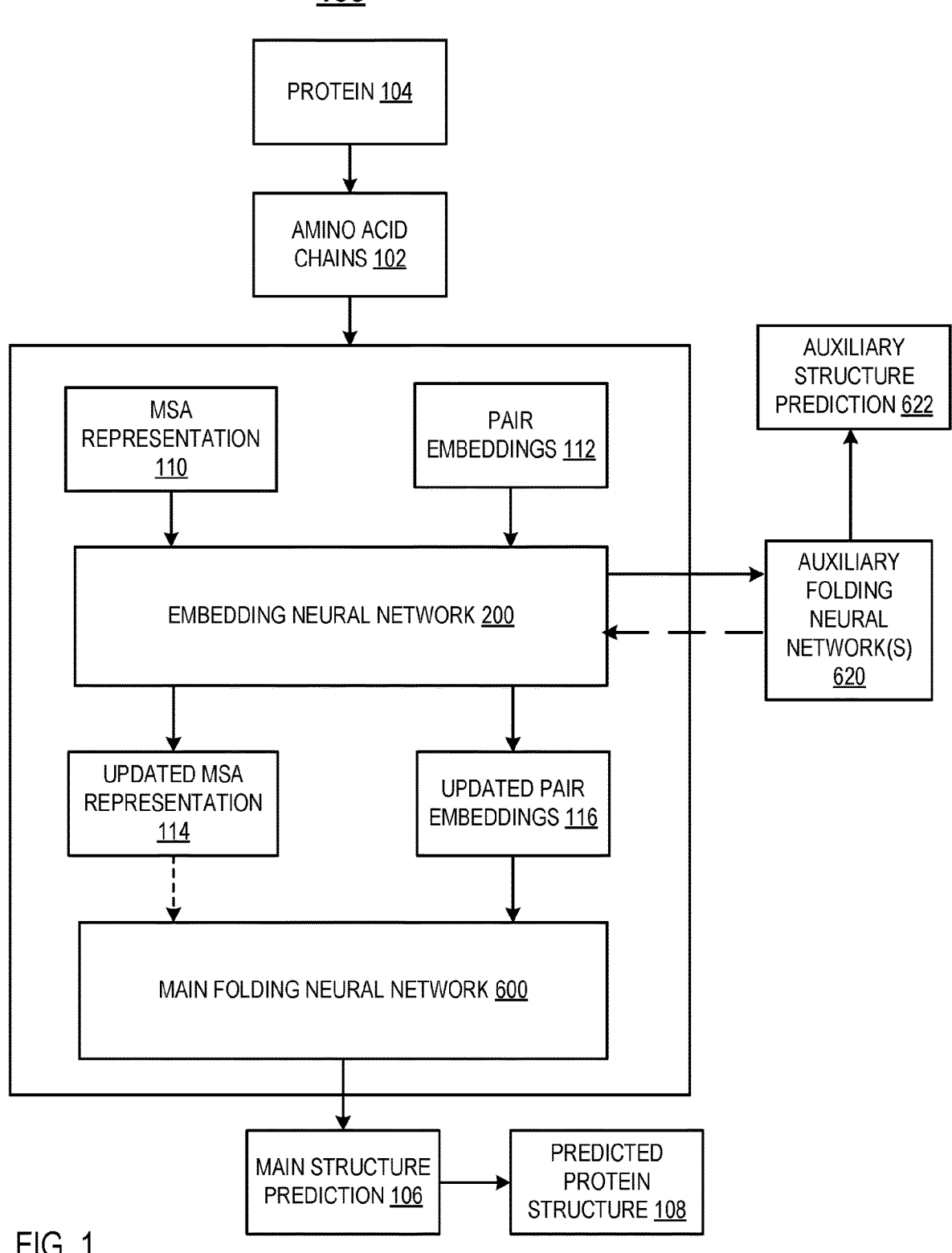
FIG. 1 shows an example protein structure prediction system.

FIG. 1 shows an example protein structure prediction system 100. The protein structure prediction system 100 is an example of a system implemented as computer programs on one or more computers in one or more locations in which the systems, components, and techniques described below are implemented.

The system 100 is configured to process data defining one or more amino acid chains 102 of a protein 104 to generate a main structure prediction 106, i.e., a set of structure parameters that define a predicted protein structure 108, i.e., a prediction of the structure of the protein 104. That is, the predicted structure 108 of the protein 104 can be defined by a set of structure parameters (e.g., included in the main structure prediction 106) that collectively define a predicted three-dimensional structure of the protein after the protein undergoes protein folding.

The structure parameters defining the predicted protein structure 108 may be as previously described. For example, they may include, e.g., location parameters and rotation parameters for each amino acid in the protein 104, a distance map that characterizes estimated distances between each pair of amino acids in the protein, a respective spatial location of each atom or backbone atom in each amino acid in the structure of the protein, or a combination thereof, as described above.

To generate the main structure prediction 106 defining the predicted protein structure 108, the system 100 may generate: (i) a multiple sequence alignment (MSA) representation 110 for the protein (in some implementations), and (ii) a set of "pair" embeddings 112 for the protein, as will be described in more detail next.

The MSA representation 110 for the protein includes a respective representation of a MSA for each amino acid chain in the protein. A MSA representation for an amino acid chain in the protein can be represented as a M×N array of embeddings (i.e., a 2-D array of embeddings having M rows and N columns), where M is the number of amino acids in the amino acid chain. Each row of the MSA representation can correspond to a respective MSA sequence for the amino acid chain in the protein. An example process for generating a MSA representation for an amino acid chain in the protein is described with reference to FIG. 10.

The system 100 generates the MSA representation 110 for the protein 104 from the MSA representations for the amino acid chains in the protein.

If the protein includes only a single amino acid chain, then the system 100 can identify the MSA representation 110 for the protein 104 as being the MSA representation for the single amino acid chain in the protein.

If the protein includes multiple amino acid chains, then the system 100 can generate the MSA representation 110 for the protein by assembling the MSA representations for the amino acid chains in the protein into a block diagonal 2-D array of embeddings, i.e., where the MSA representations for the amino acid chains in the protein form the blocks on the diagonal. The system 100 can initialize the embeddings at each position in the 2-D array outside the blocks on the diagonal to be a default embedding, e.g., a vector of zeros. The amino acid chains in the protein can be assigned an arbitrary ordering, and the MSA representations of the amino acid chains in the protein can be ordered accordingly in the block diagonal matrix. For example, the MSA representation for the first amino acid chain (i.e., according to the ordering) can be the first block on the diagonal, the MSA representation for the second amino acid chain can be the second block on the diagonal, and so on.

Generally, the MSA representation 110 for the protein can be represented as a 2-D array of embeddings. Throughout this specification, a "row" of the MSA representation for the protein refers to a row of a 2-D array of embeddings defining the MSA representation for the protein. Similarly, a "column" of the MSA representation for the protein refers to a column of a 2-D array of embeddings defining the MSA representation for the protein.

The set of pair embeddings 112 includes a respective pair embedding corresponding to each pair of amino acids in the protein 104. In general a pair embedding represents i.e. encodes information about the relationship between a pair of amino acids in the protein. A pair of amino acids refers to an ordered tuple that includes a first amino acid and a second amino acid in the protein, i.e., such that the set of possible pairs of amino acids in the protein is given by:

$$\{(A_i, A_j) : 1 \leq i, j \leq N\} \quad (1)$$

where N is the number of amino acids in the protein, $i, j \in \{1, \ldots, N\}$ index the amino acids in the protein, $A_i$ is the amino acid in the protein indexed by i, and $A_j$ is the amino acid in the protein indexed by j. If the protein includes multiple amino acid chains, then the amino acids in the protein can be sequentially indexed from $\{1, \ldots, N\}$ in accordance with the ordering of the amino acid chains in the protein. That is, the amino acids from the first amino acid chain are sequentially indexed first, followed by the amino acids from the second amino acid chain, followed by the amino acids from the third amino acid chain, and so on. The set of pair embeddings 112 can be represented as a 2-D, N×N array of pair embeddings, e.g., where the rows of the 2-D array are indexed by $i \in \{1, \ldots, N\}$, the columns of the 2-D array are indexed by $j \in \{1, \ldots, N\}$, and position (i,j) in the 2-D array is occupied by the pair embedding for the pair of amino acids $(A_i, A_j)$.

An example process for generating (initializing) a respective pair embedding corresponding to each pair of amino acids in the protein is described with reference to FIG. 11.

The system 100 generates the structure parameters defining the predicted protein structure 108 using both the MSA representation 110 and the pair embeddings 112, because both have complementary properties. The structure of the MSA representation 110 can explicitly depend on the number of amino acid chains in the MSAs corresponding to each amino acid chain in the protein. Therefore, the MSA representation 110 may be inappropriate for use in directly predicting the protein structure, because the protein structure 108 has no explicit dependence on the number of amino acids chains in the MSAs. In contrast, the pair embeddings 112 characterize relationships between respective pairs of amino acids in the protein 104 and are expressed without explicit reference to the MSAs, and are therefore a convenient and effective data representation for use in predicting the protein structure 108.

The system 100 processes the MSA representation 110 and the pair embeddings 112 using an embedding neural network 200, in accordance with the values of a set of parameters of the embedding neural network 200, to update the MSA representation 110 and the pair embeddings 112. That is, the embedding neural network 200 processes the MSA representation 110 and the pair embeddings 112 to generate an updated MSA representation 114 and updated pair embeddings 116.

The embedding neural network 200 updates the MSA representation 110 and the pair embeddings 112 by sharing information between the MSA representation 110 and the pair embeddings 112. More specifically, the embedding neural network 200 alternates between updating the current MSA representation 110 based on the current pair embeddings 112, and updating the current pair embeddings 112 based on the current MSA representation 110.

An example architecture of the embedding neural network 200 is described in more detail with reference to FIG. 2.

The system 100 generates a network input for a main folding neural network 600 from the updated pair embeddings 116, the updated MSA representation 114, or both, and processes the network input using the main folding neural network 600 to generate the main structure prediction 106, i.e., to generate the structure parameters defining the predicted protein structure.

In some implementations, the main folding neural network 600 processes the updated pair embeddings 116 to generate a distance map that includes, for each pair of amino acids in the protein, a probability distribution over a set of possible distances between the pair of amino acids in the protein structure. For example, to generate the probability distribution over the set of possible distances between a pair of amino acids in the protein structure, the folding neural network may apply one or more fully-connected neural network layers to an updated pair embedding 116 corresponding to the pair of amino acids.

In some implementations, the main folding neural network 600 generates the structure parameters by processing a network input derived from both the updated MSA representation 114 and the updated pair embeddings 116 using a geometric attention operation that explicitly reasons about the 3-D geometry of the amino acids in the protein structure. An example architecture of the main folding neural network 600 that implements a geometric attention mechanism is described with reference to FIG. 6.

A training engine trains the protein structure prediction system 100 from end-to-end to optimize a loss function that includes a term that is referred to herein as a structure loss. The training engine may train the system 100 on a set of training data including multiple training examples. Each training example may specify: (i) a training input that includes an initial MSA representation and initial pair embeddings for a protein, and (ii) a target protein structure that should be generated by the system 100 by processing the training input. Target protein structures used for training the system 100 may be determined using experimental techniques, e.g., x-ray crystallography or cryo-electron microscopy.

The structure loss may characterize a similarity between: (i) a predicted protein structure generated by the main folding neural network 600, and (ii) the target protein structure that should have been generated by the main folding neural network 600.

For example, if the predicted structure parameters define predicted location parameters and predicted rotation parameters for each amino acid in the protein, then the structure loss $\mathcal{L}_{structure}$ may be given by:

$$\mathcal{L}_{structure} = \frac{1}{N^2}\sum_{i,j=1}^{N}\left(1 - \frac{|t_{ij}-\widetilde{t_{ij}}|}{A}\right)_+ \tag{2}$$

$$t_{ij} = R_i^{-1}(t_j - t_i) \tag{3}$$

$$\widetilde{t_{ij}} = \tilde{R}_i^{-1}(\tilde{t}_j - \tilde{t}_i) \tag{4}$$

where N is the number of amino acids in the protein, $t_i$ denote the predicted location parameters for amino acid i, $R_i$ denotes a 3×3 rotation matrix specified by the predicted rotation parameters for amino acid i, $\tilde{t}_i$ are the target location parameters for amino acid i, $\tilde{R}_i$ denotes a 3×3 rotation matrix specified by the target rotation parameters for amino acid i, A is a constant, $$R_i^{-1}$$

refers to the inverse of the 3×3 rotation matrix specified by predicted rotation parameters $R_i$, $$\tilde{R}_i^{-1}$$

refers to the inverse of the 3×3 rotation matrix specified by the target rotation parameters $\tilde{R}_i$, and $(\cdot)_+$ denotes a rectified linear unit (ReLU) operation.

The structure loss defined with reference to equations (2)-(4) may be understood as averaging the loss $|t_{ij}-\widetilde{t_{ij}}|$ over each pair of amino acids in the protein. The term $t_{ij}$ defines the predicted spatial location of amino acid j in the predicted frame of reference of amino acid i, and $\widetilde{t_{ij}}$ defines the actual spatial location of amino acid j in the actual frame of reference of amino acid i. These terms are sensitive to the predicted and actual rotations of amino acid i and j, and therefore carry richer information than loss terms that are only sensitive to the predicted and actual distances between amino acids.

As another example, if the predicted structure parameters define predicted spatial locations of each atom in each amino acid of the protein, then the structure loss may be an average error (e.g., squared-error) between: (i) the predicted spatial locations of the atoms, and (ii) the target (e.g., ground truth) spatial locations of the atoms.

Optimizing the structure loss encourages the system 100 to generate predicted protein structures that accurately approximate true protein structures.

In addition to optimizing the structure loss, the training engine may train the system 100 to optimize one or more auxiliary losses, i.e., the loss function can include additional terms corresponding to each of the auxiliary losses. The auxiliary losses may penalize predicted structures having characteristics that are unlikely to occur in the natural world, e.g., based on the bond angles and/or bond lengths of the bonds between the atoms in the amino acids in the predicted structures, or based on the proximity of the atoms in different amino acids in the predicted structures.

The training engine may train the structure prediction system 100 on the training data over multiple training iterations, e.g., using stochastic gradient descent training techniques.

Additionally, at least during training, the system 100 also includes one or more auxiliary folding neural networks 620. Each auxiliary folding neural network 620 generally has the same architecture as the main folding neural network 600 and generates a respective auxiliary structure prediction 622 that is the same type of output as the main structure prediction 106, but based on different information.

In particular, as will be described in more detail below, each auxiliary folding neural network 620 receives an input that includes a different intermediate output of the embedding neural network 200, i.e., instead of the updated pair embeddings 116 (and optionally the updated MSA representation 114), each auxiliary folding neural network receives as input a different intermediate set of pair embeddings (and optionally a corresponding intermediate MSA representation).

Each auxiliary folding neural network 620 processes an input generated from the intermediate output received by the network 620 to generate an auxiliary structure prediction 622 that, like the main structure prediction 106, predicts the structure of the input protein.

To account for the inclusion of the auxiliary folding neural network(s) 620, the training engine augments the loss function to include a respective additional structure loss term for each auxiliary folding neural network 620. The structure loss term for each neural network 620 characterizes the similarity between: (i) a predicted protein structure generated by the auxiliary folding neural network 620 and (ii) the target protein structure that should have been generated by the system. Each auxiliary structure loss term will generally be of the same form as the structure loss used to evaluate the main structure prediction 106 generated by the main folding neural network 600, i.e., one of the structure losses described above.

During the training, the training engine backpropagates gradients of each auxiliary structure loss term into the embedding neural network 200, so that the parameters of those components of the embedding neural network 200 that participated in generating the intermediate output are updated based on the gradients of the auxiliary structure loss term in addition to the main structure loss term. In other words, the auxiliary structure prediction generated by any given auxiliary folding neural network 620 is used to update the parameter values of the parameters of the given auxiliary folding neural network 620 and of the components of the embedding neural network 200 upon which the generation of the intermediate output that used by the given folding neural network 620 to generate the auxiliary structure prediction is conditioned.

Optionally, each of the auxiliary structure loss terms can be assigned a lower weight in the overall loss function than the main structure loss, i.e., so that gradient signals generated as a result of the main structure prediction are given more weight than gradient signals generated as a result of any given auxiliary structure prediction.

In some implementations, the training engine places constraints on the values of the parameters of the auxiliary neural network(s) 620 during the training. As one example, the training engine can constrain the values of the parameters of the auxiliary neural network(s) 620 so that the networks 620 share parameter values, i.e., constrain the value of any given parameter to be the same for all of the auxiliary neural networks 620. As another example, the training engine can constrain the values of the parameters of the auxiliary neural network(s) 620 and the main folding network 600 so that the networks 620 and the network 600 share parameter values, i.e., constrain the value of any given parameter to be the same for all of the auxiliary neural networks 620 and for the main folding network 600.

Optionally, the training engine can also make use of additional auxiliary losses when training the neural networks. In particular, the description of FIG. 6 below describes an additional auxiliary loss that can be computed based on intermediate structure parameters generated by the main folding network 600. The same auxiliary loss can also be applied to the intermediate structure parameters generated by each auxiliary folding network 620.

Optionally, the auxiliary neural network(s) 620 can also be included as part of the system 100 after training. In these cases, each auxiliary folding neural network 620 uses the predicted output 622 generated by the neural network 620 to update the intermediate output of the embedding neural network 200 that was received as input by the auxiliary folding neural network 620. The auxiliary neural network then provides the updated intermediate output to the embedding neural network for further processing, i.e., instead of the original intermediate output. Thus, in these cases, the predictions made by the auxiliary folding neural network(s) 620 can be used to improve the quality of the updated embeddings generated by the embedding neural network 200 that are provided as input to the main folding neural network 600.

In some implementations, instead of or in addition to feeding back the prediction 622 made by any given auxiliary folding neural network 620, the neural network 620 can provide features generated by the network 620 as part of generating the prediction 622 to the embedding neural network. In particular, the neural network 620 can select any appropriate intermediate output generated by the network 620, transform that output into features, and then feed the features back into the embedding neural network.

Figure 2:
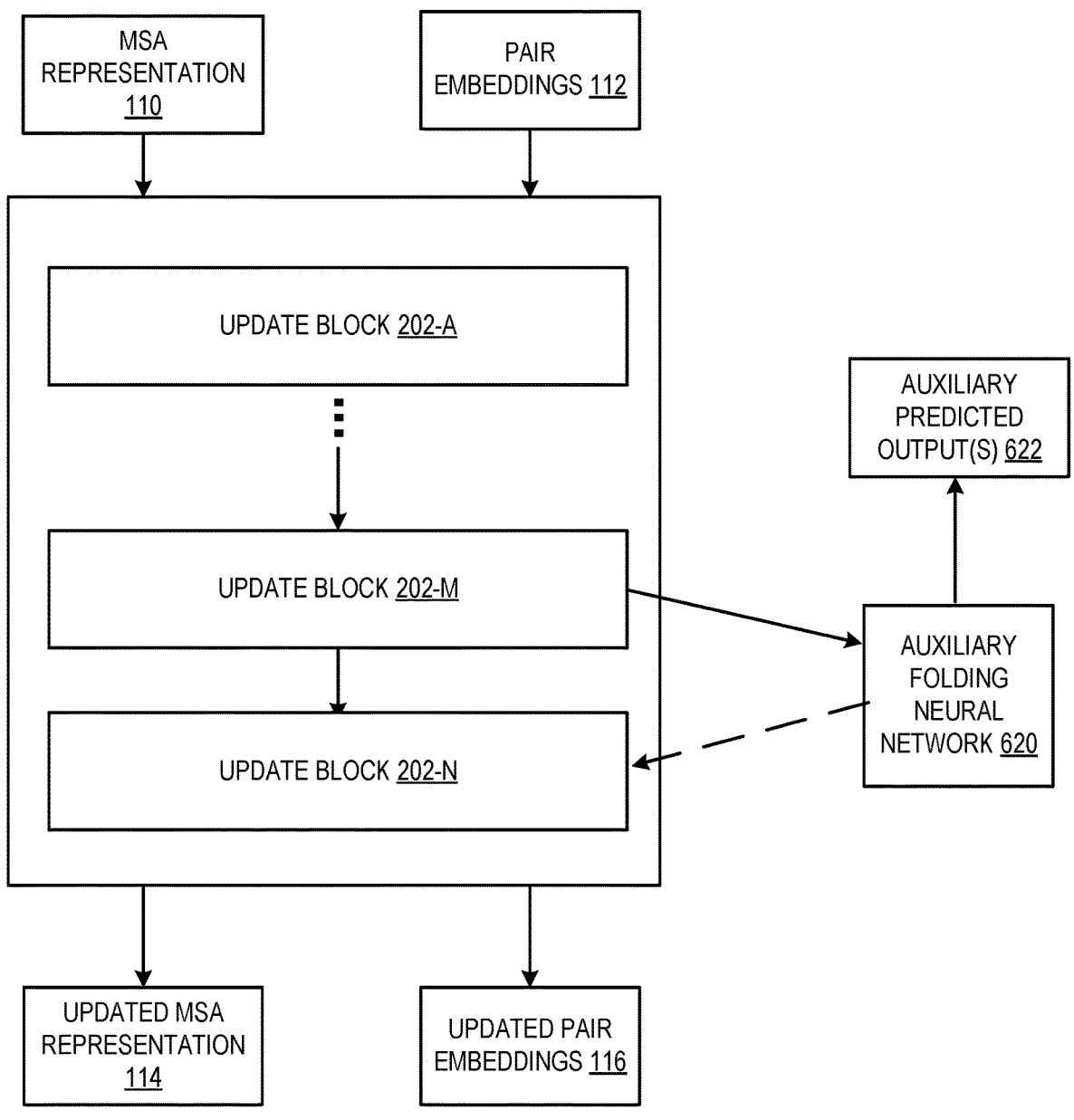
FIG. 2 shows an example architecture of an embedding neural network.

FIG. 2 shows an example architecture of an embedding neural network 200 that is configured to process the MSA representation 110 and the pair embeddings 112 to generate the updated MSA representation 114 and the updated pair embeddings 116.

The embedding neural network 200 includes a sequence of update blocks 202-A-N. Throughout this specification, a "block" refers to a portion of a neural network, e.g., a subnetwork of the neural network that includes one or more neural network layers.

Each update block in the embedding neural network is configured to receive a block input that includes a MSA representation and a pair embedding, and to process the block input to generate a block output that includes an updated MSA representation and an updated pair embedding.

In particular, while the description of FIG. 2 and of the Figures that follow describes an architecture of the embedding neural network 200 where each block updates both the pair embeddings and the MSA representation, the described techniques for incorporating auxiliary folding neural networks into a structure prediction system can be employed with any appropriate architecture of the embedding neural network that includes multiple blocks that each update the pair embeddings. As a particular example of an alternative architecture to the one described below, the embedding neural network 200 can employ an architecture in which the pair embeddings 112 are initialized using the MSA representation 110 as described above, and in which each block receives only the current pair embeddings and updates those embeddings by applying self-attention as described below, but without the dependence on the MSA representation.

The embedding neural network 200 provides the MSA representation 110 and the pair embeddings 112 included in the network input of the embedding neural network 200 to the first update block (i.e., in the sequence of update blocks). The first update block processes the MSA representation 110 and the pair embeddings 112 to generate an updated MSA representation and updated pair embeddings.

For each update block after the first update block, the embedding neural network 200 provides the update block with the MSA representation and the pair embeddings generated by the preceding update block, and for each update block except the last update block it provides the updated MSA representation and the updated pair embeddings generated by the update block to the next update block.

The embedding neural network 200 gradually enriches the information content of the MSA representation 110 and the pair embeddings 112 by repeatedly updating them using the sequence of update blocks 202-A-N.

The embedding neural network 200 may provide the updated MSA representation 114 and the updated pair embeddings 116 generated by the final update block (i.e., in the sequence of update blocks) as the network output.

As shown in FIG. 2, the system also includes a single auxiliary folding neural network 620 that corresponds to update block 202-M (where block 202-M is any update block in the sequence of update blocks; in some implementations, it may be the first update block 202-A but it is generally not the last update block 202-N) and generates an auxiliary structure prediction 622. The auxiliary folding neural network 620 receives as input at least the updated pair embeddings generated by the corresponding update block, i.e., the update block 202-M, and uses those updated pair embeddings to generate the auxiliary structure prediction 622. Optionally, as described above, the auxiliary folding neural network 620 may also receive the updated MSA representation as generated by the update block 202-M. The auxiliary folding network 620 can generate the prediction 622 in any of the ways described above and below with reference to main folding network 600.

During training, the training engine uses the structure loss computed from the auxiliary structure prediction 622 to update, through backpropagation, the parameter values of the auxiliary folding neural network 620 and the parameter values of the update block 202M and the update blocks that precede the update block 202M in the sequence of update blocks, i.e., the update blocks 202A-L. Including this signal as part of the gradient signals that are backpropagated through the system can provide richer feedback to the update blocks and result in a higher quality final outputs being generated by the embedding neural network 200.

While only a single auxiliary folding network 620 is shown in FIG. 2, the system can include multiple auxiliary neural networks 620, each corresponding to a different one of the update blocks. As some examples, each update block can have a corresponding auxiliary neural network 620, every other update block in the sequence can have a corresponding auxiliary neural network 620, or only update blocks that are after a particular position in the sequence can have corresponding auxiliary neural networks 620.

Thus, more generally, each of the auxiliary neural networks 620 corresponds to a different one of the update blocks and receives as input at least the updated pair embeddings that are generated by the corresponding update block. Each auxiliary folding network 620 uses the received input to generate an auxiliary structure prediction and the training engine uses a loss computed from the auxiliary structure prediction to update the parameter values of the auxiliary neural network, the corresponding update block, and any update blocks that precede the corresponding update block in the sequence of update blocks through backpropagation.

In some implementations, the auxiliary neural network(s) 620 are not used after training of the system is complete.

In other implementations, the auxiliary neural network(s) 620 remain part of the system after training. In these implementations, both during training and after training, i.e., at inference, each auxiliary folding network 620 uses the prediction 622 generated by the network 620 to further update the pair embeddings that are received as input by the network 620 from the corresponding update block. The auxiliary folding network 620 then provides these further updated pair embeddings as input to the update block that is immediately after the corresponding update block in the sequence, i.e., instead of the updated embeddings as initially generated by the corresponding update block.

In the example of FIG. 2, the auxiliary folding network 620 updates the pair embeddings received from the update block 202-M and provides the further updated pair embeddings as input to the next update block, i.e., the update block 202-N, in place of the pair embeddings generated by the update block 202-M.

The auxiliary folding network 620 can update the pair embeddings received from the update block 202-M using the auxiliary structure prediction 622 in any of a variety of ways.

Generally, however, the network 620 transforms the structure prediction 622 into embeddings that have the same dimensionality as the updated pair embeddings and then combines the transformed structure prediction with the updated pair embeddings to generate the further updated pair embeddings.

In some implementations, the network 620 directly combines the transformed structure prediction and the updated pair embeddings, e.g., the network 620 adds, averages, or concatenates the transformed structure prediction and the updated pair embeddings.

In some other implementations, the network 620 can combine the updated pair embedding and the transformed structure prediction by applying a learned combination, i.e., that is learned jointly with the training of the embedding neural network and the main folding neural network. As a particular example, the network 620 can apply a learned cross-attention mechanism to incorporate information from the transformed structure prediction. Unlike the self-attention mechanism described below, in a cross-attention mechanism the queries are generated from the updated pair embedding while the keys and values are generated from the transformed structure prediction.

In particular, as described above, in some implementations, the auxiliary structure prediction 622 is a distance map that characterizes a respective estimated distance between each pair of amino acids in the protein. In these cases, the network 620 can project the distance map to the same dimensionality as the updated pair embeddings to generate the transformed structure prediction.

For example, the system can discretize each distance in the distance map by assigning each distance to a bin from a plurality of bins that each correspond to a different range of distance values. The system can then embed each discretized distance, e.g., by multiplying a one hot encoded representation of the discretized distance by an embedding matrix. A one hot encoded representation represents the discretized distance as a vector that includes a "1" in the position corresponding to the discretized distance and a "0" at all other positions corresponding to all other discretized distances.

As another example, the system can apply a kernel function to each distance in the distance map to generate a representation of the distance and then embed the representations. For example the kernel function can be equal to or, more generally, directly proportional to the function exp(-distance).

As another example, as described above, in some other implementations, the auxiliary structure prediction 622 includes structure parameters that define the position of a specified atom in each amino acid in the protein. The network 620 can construct, based on the positions defined by the structure parameters, a distance map by computing the distances between pairs of the specified atoms in the amino acids in the protein. In these cases, the network 620 can project the distance map to the same dimensionality as the updated pair embeddings to generate the transformed structure prediction as described above.

Figure 3:
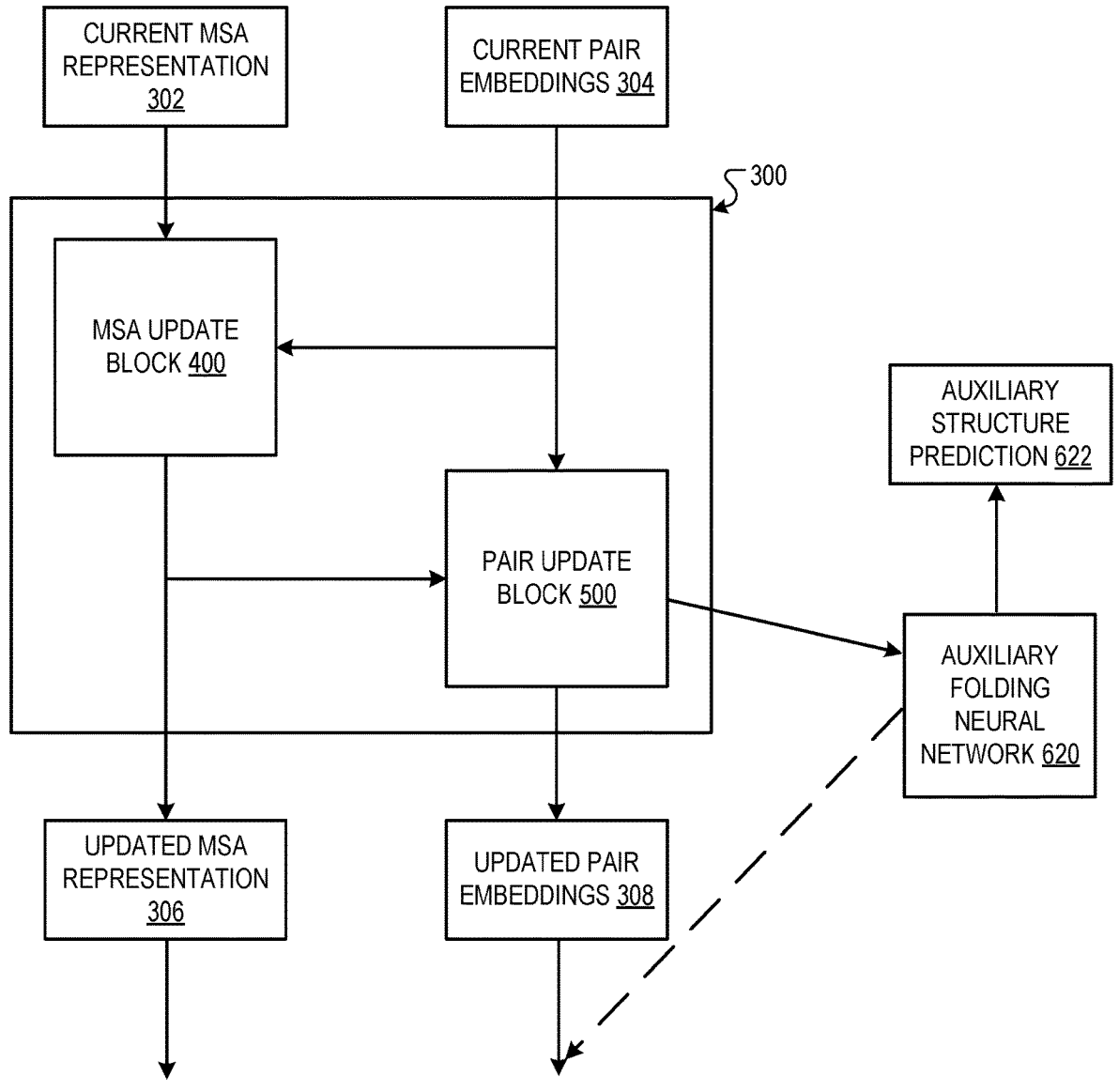
FIG. 3 shows an example architecture of an update block of the embedding neural network.

FIG. 3 shows an example architecture of an update block 300 of the embedding neural network 200, i.e., as described with reference to FIG. 2.

The update block 300 receives a block input that includes the current MSA representation 302 and the current pair embeddings 304, and processes the block input to generate the updated MSA representation 306 and the updated pair embeddings 308.

The update block 300 includes an MSA update block 400 and a pair update block 500.

The MSA update block 400 updates the current MSA representation 302 using the current pair embeddings 304, and the pair update block 500 updates the current pair embeddings 304 using the updated MSA representation 306 (i.e., that is generated by the MSA update block 400).

Generally, the MSA representation and the pair embeddings can encode complementary information. For example, the MSA representation can encode information about the correlations between the identities of the amino acids in different positions among a set of evolutionarily-related amino acid chains, and the pair embeddings can encode information about the inter-relationships between the amino acids in the protein. The MSA update block 400 enriches the information content of the MSA representation using complementary information encoded in the pair embeddings, and the pair update block 500 enriches the information content of the pair embeddings using complementary information encoded in the MSA representation. As a result of this enrichment, the updated MSA representation and the updated pair embedding encode information that is more relevant to predicting the protein structure.

The update block 300 is described herein as first updating the current MSA representation 302 using the current pair embeddings 304, and then updating the current pair embeddings 304 using the updated MSA representation 306. The description should not be understood as limiting the update block to performing operations in this sequence, e.g., the update block could first update the current pair embeddings using the current MSA representation, and then update the current MSA representation using the updated pair embeddings.

The update block 300 is described herein as including an MSA update block 400 (i.e., that updates the current MSA representation) and a pair update block 500 (i.e., that updates the current pair embeddings). The description should not be understood to limiting the update block 300 to include only one MSA update block or only one pair update block. For example, the update block 300 can include multiple MSA update blocks that update the MSA representation multiple times before the MSA representation is provided to a pair update block for use in updating the current pair embeddings. As another example, the update block 300 can include multiple pair update blocks that update the pair embeddings multiple times using the MSA representation.

The MSA update block 400 and the pair update block 500 can have any appropriate architectures that enable them to perform their described functions.

In some implementations, the MSA update block 400, the pair update block 500, or both, include one or more "self-attention" blocks. As used throughout this document, a self-attention block generally refers to a neural network block that updates a collection of embeddings, i.e., that receives a collection of embeddings and outputs updated embeddings. To update a given embedding, the self-attention block can determine a respective "attention weight" between the given embedding and each of one or more selected embeddings, and then update the given embedding using: (i) the attention weights, and (ii) the selected embeddings. For convenience, the self-attention block may be said to update the given embedding using attention "over" the selected embeddings.

For example, a self-attention block may receive a collection of input embeddings $$\{x_i\}_{i=1}^{N},$$

where N is the number of amino acids in the protein, and to update embedding $x_i$, the self-attention block may determine attention weights $$[a_{i,j}]_{j=1}^{N}$$

where $a_{i,j}$ denotes the attention weight between $x_i$ and $x_j$, as:

$$[a_{i,j}]_{j=1}^{N} = \text{softmax}\left(\frac{(W_q x_i)K^T}{c}\right) \quad (5)$$

$$K^T = [W_k x_j]_{j=1}^{N} \quad (6)$$

where $W_q$ and $W_k$ are learned parameter matrices, softmax($\cdot$) denotes a soft-max normalization operation, and c is a constant. Using the attention weights, the self-attention layer may update embedding $x_i$ as:

$$x_i \leftarrow \sum_{j=1...N} a_{i,j} \cdot (W_v x_j) \tag{7}$$

where $W_v$ is a learned parameter matrix. ($W_q x_i$ can be referred to as the "query embedding" for input embedding $x_i$, $W_k x_j$ can be referred to as the "key embedding" for input embedding $x_i$, and $W_v x_j$ can be referred to as the "value embedding" for input embedding $x_i$).

The parameter matrices $W_q$ (the "query embedding matrix"), $W_k$ (the "key embedding matrix"), and $W_v$ (the "value embedding matrix") are trainable parameters of the self-attention block. The parameters of any self-attention blocks included in the MSA update block 400 and the pair update block 500 can be understood as being parameters of the update block 300 that can be trained as part of the end-to-end training of the protein structure prediction system 100 described with reference to FIG. 1. Generally, the (trained) parameters of the query, key, and value embedding matrices are different for different self-attention blocks, e.g., such that a self-attention block included in the MSA update block 400 can have different query, key, and value embedding matrices with different parameters than a self-attention block included in the pair update block 500.

In some implementations, the MSA update block 400, the pair update block 500, or both, include one or more self-attention blocks that are conditioned on the pair embeddings, i.e., that implement self-attention operations that are conditioned on the pair embeddings. To condition a self-attention operation on the pair embeddings, the self-attention block can process the pair embeddings to generate a respective "attention bias" corresponding to each attention weight. For example, in addition to determining the attention weights $$[a_{i,j}]_{j=1}^{N}$$

in accordance with equations (5)-(6), the self-attention block can generate a corresponding set of attention biases $$[b_{i,j}]_{j=1}^{N},$$

where $b_{i,j}$ denotes the attention bias between $x_i$ and $x_j$. The self-attention block can generate the attention bias $b_{i,j}$ by applying a learned parameter matrix to the pair embedding $h_{i,j}$, i.e., for the pair of amino acids in the protein indexed by (i,j).

The self-attention block can determine a set of "biased attention weights"

$$[c_{i,j}]_{j=1}^{N},$$

where $c_{i,j}$ denotes the biased attention weight between $x_i$ and $x_j$, e.g., by summing (or otherwise combining) the attention weights and the attention biases. For example, the self-attention block can determine the biased attention weight $c_{i,j}$ between embeddings $x_i$ and $x_j$ as:

$$c_{i,j}=a_{i,j}+b_{i,j}$$

where $a_{i,j}$ is the attention weight between $x_i$ and $x_j$ and $b_{i,j}$ is the attention bias between $x_i$ and $x_j$. The self-attention block can update each input embedding $x_i$ using the biased attention weights, e.g.:

$$x_i \leftarrow \sum_{j=1...N} c_{i,j} \cdot (W_v x_j) \tag{8}$$

where $W_v$ is a learned parameter matrix.

Generally, the pair embeddings encode information characterizing the structure of the protein and the relationships between the pairs of amino acids in the structure of the protein. Applying a self-attention operation that is conditioned on the pair embeddings to a set of input embeddings allows the input embeddings to be updated in a manner that is informed by the protein structural information encoded in the pair embeddings. The update blocks of the embedding neural network can use the self-attention blocks that are conditioned on the pair embeddings to update and enrich the MSA representation and the pair embeddings themselves.

Optionally, a self-attention block can have multiple "heads" that each generate a respective updated embedding corresponding to each input embedding, i.e., such that each input embedding is associated with multiple updated embeddings. For example, each head may generate updated embeddings in accordance with different values of the parameter matrices $W_q$, $W_k$, and $W_v$ that are described with reference to equations (5)-(7). A self-attention block with multiple heads can implement a "gating" operation to combine the updated embeddings generated by the heads for an input embedding, i.e., to generate a single updated embedding corresponding to each input embedding. For example, the self-attention block can process the input embeddings using one or more neural network layers (e.g., fully connected neural network layers) to generate a respective gating value for each head. The self-attention block can then combine the updated embeddings corresponding to an input embedding in accordance with the gating values. For example, the self-attention block can generate the updated embedding for an input embedding $x_i$ as:

$$\sum_{k=1}^{K} \alpha_k \cdot x_i^{next} \tag{9}$$

where k indexes the heads, $a_k$ is the gating value for head k, and $$x_i^{next}$$

is the updated embedding generated by head k for input embedding $x_i$.

An example architecture of a MSA update block 400 that uses self-attention blocks conditioned on the pair embeddings is described with reference to FIG. 4. The example MSA update block described with reference to FIG. 4 updates the current MSA representation based on the current pair embeddings by processing the rows of the current MSA representation using a self-attention block that is conditioned on the current pair embeddings.

An example architecture of a pair update block 500 that uses self-attention blocks conditioned on the pair embeddings is described with reference to FIG. 5. The example pair update block described with reference to FIG. 5 updates the current pair embeddings based on the updated MSA representation by computing an outer product mean of the updated MSA representation, adding the result of the outer product mean to the current pair embeddings, and processing the current pair embeddings using self-attention blocks that are conditioned on the current pair embeddings.

As shown in FIG. 3, the update block 300 has a corresponding auxiliary folding network 620. The auxiliary folding network 620 receives as input the updated pair embeddings 308 generated by the pair update block 500 (and optionally the updated MSA representation 306 generated by the MSA update 400) and, as described above, generates an auxiliary structure prediction 622 from the received input. The auxiliary structure prediction 622 is then used by the training engine to update the parameter values of the auxiliary folding network 600, the components of the update block 300, and the components of any blocks preceding the update block 300 in the sequence of update blocks.

In implementations in which the auxiliary folding network 620 is also used during training, the auxiliary folding network 620 also uses the auxiliary structure prediction 620 to further update the updated pair embeddings 308 before the pair embedding are provided to the next block, i.e., so that the pair embeddings that are provided to the next block in the sequence are further updated pair embeddings that are a combination of the updated pair embeddings 308 and the transformed structure prediction as described above.

Figure 4:
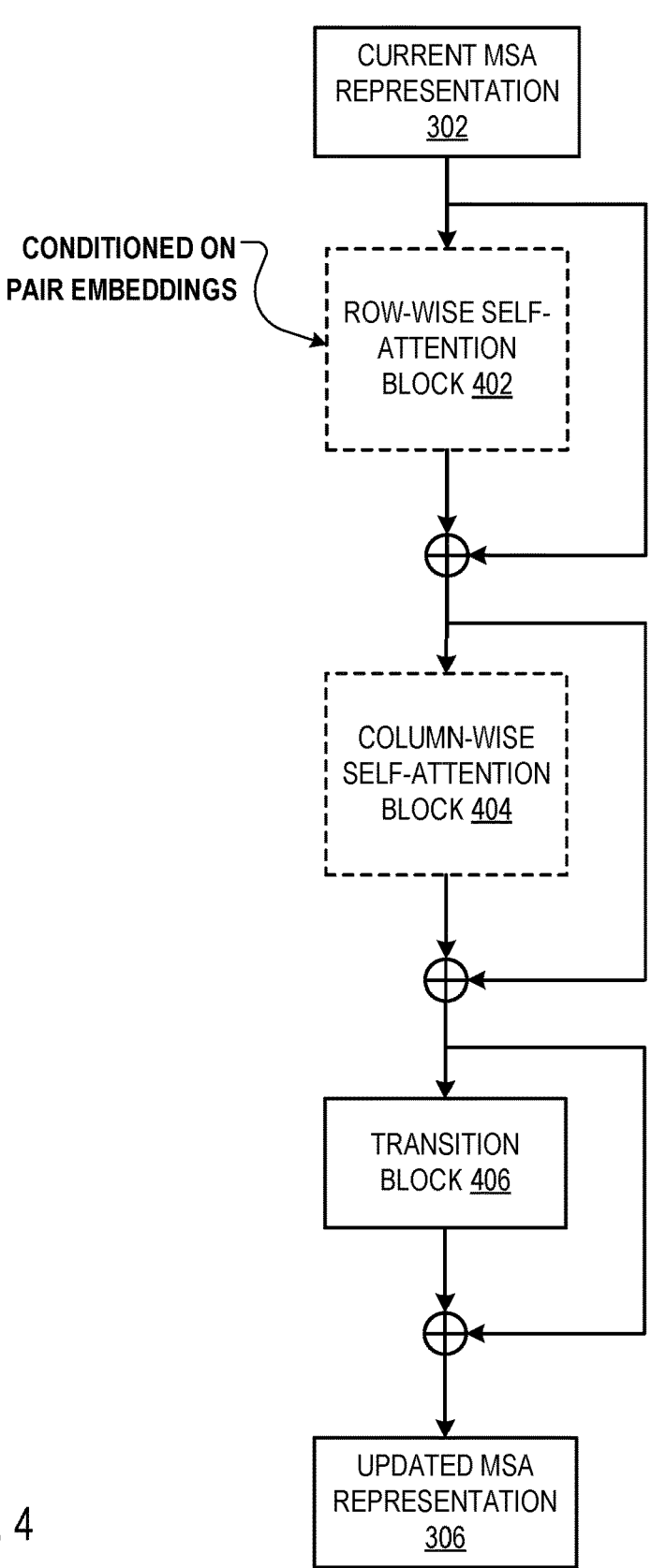
FIG. 4 shows an example architecture of a MSA update block.

FIG. 4 shows an example architecture of a MSA update block 400. The MSA update block 400 is configured to receive the current MSA representation 302, to update the current MSA representation 306 based (at least in part) on the current pair embedding.

To update the current MSA representation 302, the MSA update block 400 updates the embeddings in each row of the current MSA representation using a self-attention operation (i.e., a "row-wise" self-attention operation) that is conditioned on the current pair embeddings. More specifically, the MSA update block 400 provides the embeddings in each row of the current MSA representation 302 to a "row-wise" self-attention block 402 that is conditioned on the current pair embeddings, e.g., as described with reference to FIG. 3, to generate updated embeddings for each row of the current MSA representation 302. Optionally, the MSA update block can add the input to the row-wise self-attention block 402 to the output of the row-wise self-attention block 402. Conditioning the row-wise self-attention block 402 on the current pair embeddings enables the MSA update block 400 to enrich the current MSA representation 302 using information from the current pair embeddings.

The MSA update block then updates the embeddings in each column of the current MSA representation using a self-attention operation (i.e., a "column-wise" self-attention operation) that is not conditioned on the current pair embeddings. More specifically, the MSA update block 400 provides the embeddings in each column of the current MSA representation 302 to a "column-wise" self-attention block 404 that is not conditioned on the current pair embeddings to generate updated embeddings for each column of the current MSA representation 302. As a result of not being conditioned on the current pair embeddings, the column-wise self-attention block 404 generates updated embeddings for each column of the current MSA representation using attention weights (e.g., as described with reference to equations (5)-(6)) rather than biased attention weights (e.g., as described with reference to equation (8)). Optionally, the MSA update block can add the input to the column-wise self-attention block 404 to the output of the column-wise self-attention block 404.

The MSA update block then processes the current MSA representation 302 using a transition block, e.g., that applies one or more fully-connected neural network layers to the current MSA representation 302. Optionally, the MSA update block 400 can add the input to the transition block 406 to the output of the transition block 406.

The MSA update block can output the updated MSA representation 306 resulting from the operations performed by the row-wise self-attention block 402, the column-wise self-attention block 404, and the transition block 406.

Figure 5:
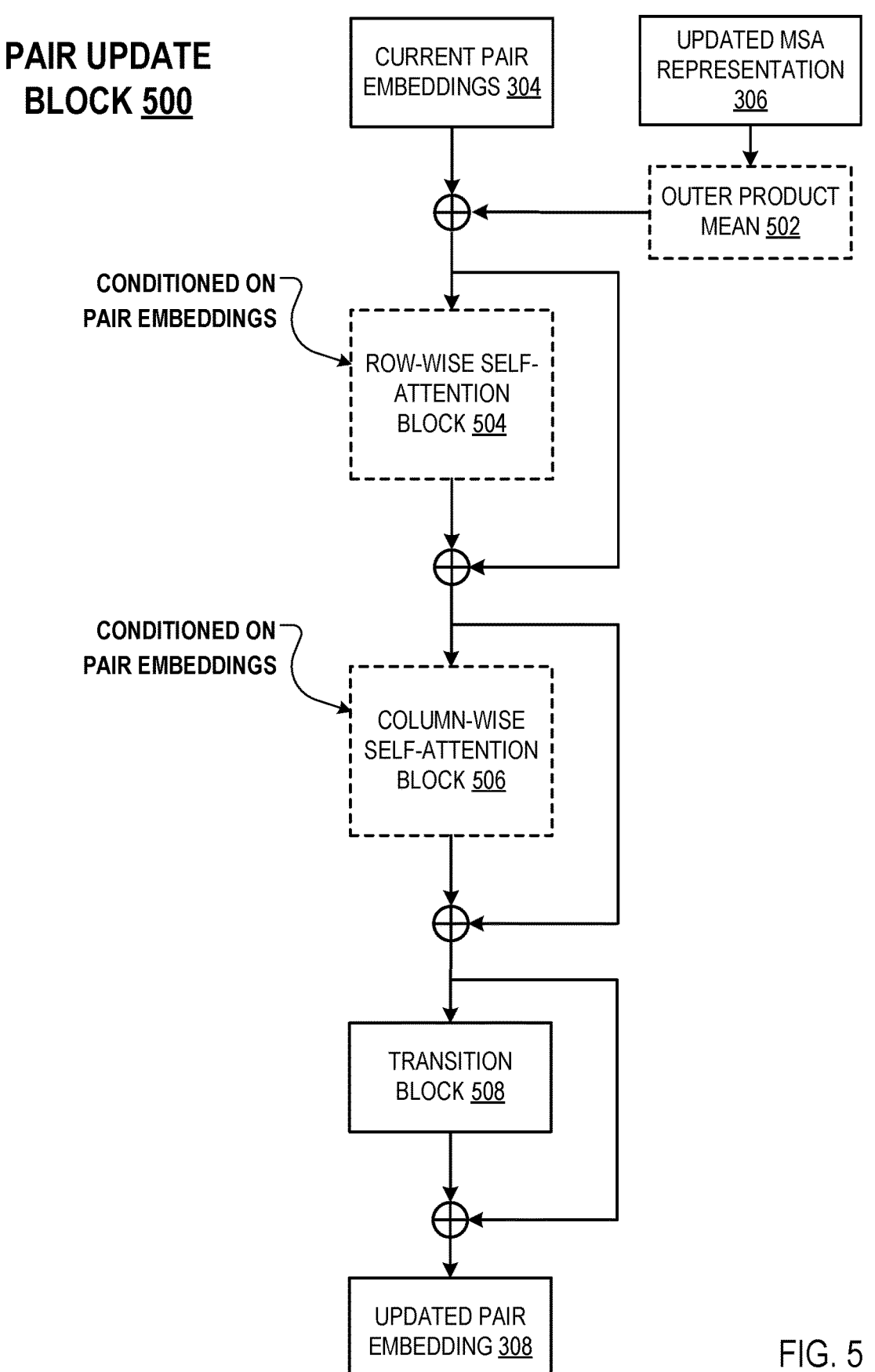
FIG. 5 shows an example architecture of a pair update block.

FIG. 5 shows an example architecture of a pair update block 500. The pair update block 500 is configured to receive the current pair embeddings 304, and to update the current pair embeddings 304 based (at least in part) on the updated MSA representation 306.

To update the current pair embeddings 304, the pair update block 500 applies an outer product mean operation 502 to the updated MSA representation 306 and adds the result of the outer-product mean operation 502 to the current pair embeddings 304.

The outer product mean operation defines a sequence of operations that, when applied to an MSA representation represented as an M×N array of embeddings, generates an N×N array of embeddings, i.e., where N is the number of amino acids in the protein. The current pair embeddings 304 can also be represented as an N×N array of embeddings, and adding the result of the outer product mean 502 to the current pair embeddings 304 refers to summing the two N×N arrays of embeddings.

To compute the outer product mean, the pair update block generates a tensor $A(\cdot)$, e.g., given by:

$$A(res1, res2, ch1, ch2) =$$

$$\frac{1}{|rows|} \sum_{rows} LeftAct(row, res1, ch1) \cdot RightAct(row, res2, ch2)$$

where $res1, res2 \in \{1, \dots, N\}$, $ch1, ch2 \in \{1, \dots, C\}$, where C is the number of channels in each embedding of the MSA representation, |rows| is the number rows in the MSA representation, LeftAct(row,res1,ch1) is a linear operation (e.g., defined by a matrix multiplication) applied to the channel ch1 of the embedding of the MSA representation located at the row indexed by "row" and the column indexed by "res1", and RightAct(row,res2,ch2) is a linear operation (e.g., defined by a matrix multiplication) applied to the channel ch2 of the embedding of the MSA representation located at the row indexed by "row" and the column indexed by "res2". The result of the outer product mean is generated by flattening and linearly projecting the (ch1,ch2) dimensions of the tensor A. Optionally, the pair update block can perform one or more Layer Normalization operations (e.g., as described with reference to Jimmy Lei Ba et al., "Layer Normalization," arXiv:1607.06450) as part of computing the outer product mean.

Generally, the updated MSA representation 306 encodes information about the correlations between the identities of the amino acids in different positions among a set of evolutionarily-related amino acid chains. The information encoded in the updated MSA representation 306 is relevant to predicting the structure of the protein, and by incorporating the information encoded in the updated MSA representation into the current pair embeddings (i.e., by way of the outer product mean 502), the pair update block 500 can enhance the information content of the current pair embeddings.

After updating the current pair embeddings 304 using the updated MSA representation (i.e., by way of the outer product mean 502), the pair update block 500 updates the current pair embeddings in each row of an arrangement of the current pair embeddings into an N×N array using a self-attention operation (i.e., a "row-wise" self-attention operation) that is conditioned on the current pair embeddings. More specifically, the pair update block 500 provides each row of current pair embeddings to a "row-wise" self-attention block 504 that is also conditioned on the current pair embeddings, e.g., as described with reference to FIG. 3, to generate updated pair embeddings for each row. Optionally, the pair update block can add the input to the row-wise self-attention block 504 to the output of the row-wise self-attention block 504.

The pair update block 500 then updates the current pair embeddings in each column of the N×N array of current pair embeddings using a self-attention operation (i.e., a "column-wise" self-attention operation) that is also conditioned on the current pair embeddings. More specifically, the pair update block 500 provides each column of current pair embeddings to a "column-wise" self-attention block 506 that is also conditioned on the current pair embeddings to generate updated pair embeddings for each column. Optionally, the pair update block can add the input to the column-wise self-attention block 506 to the output of the column-wise self-attention block 506.

The pair update block 500 then processes the current pair embeddings using a transition block, e.g., that applies one or more fully-connected neural network layers to the current pair embeddings. Optionally, the pair update block 500 can add the input to the transition block 508 to the output of the transition block 508.

The pair update block can output the updated pair embeddings 308 resulting from the operations performed by the row-wise self-attention block 504, the column-wise self-attention block 506, and the transition block 508.

Figure 6:
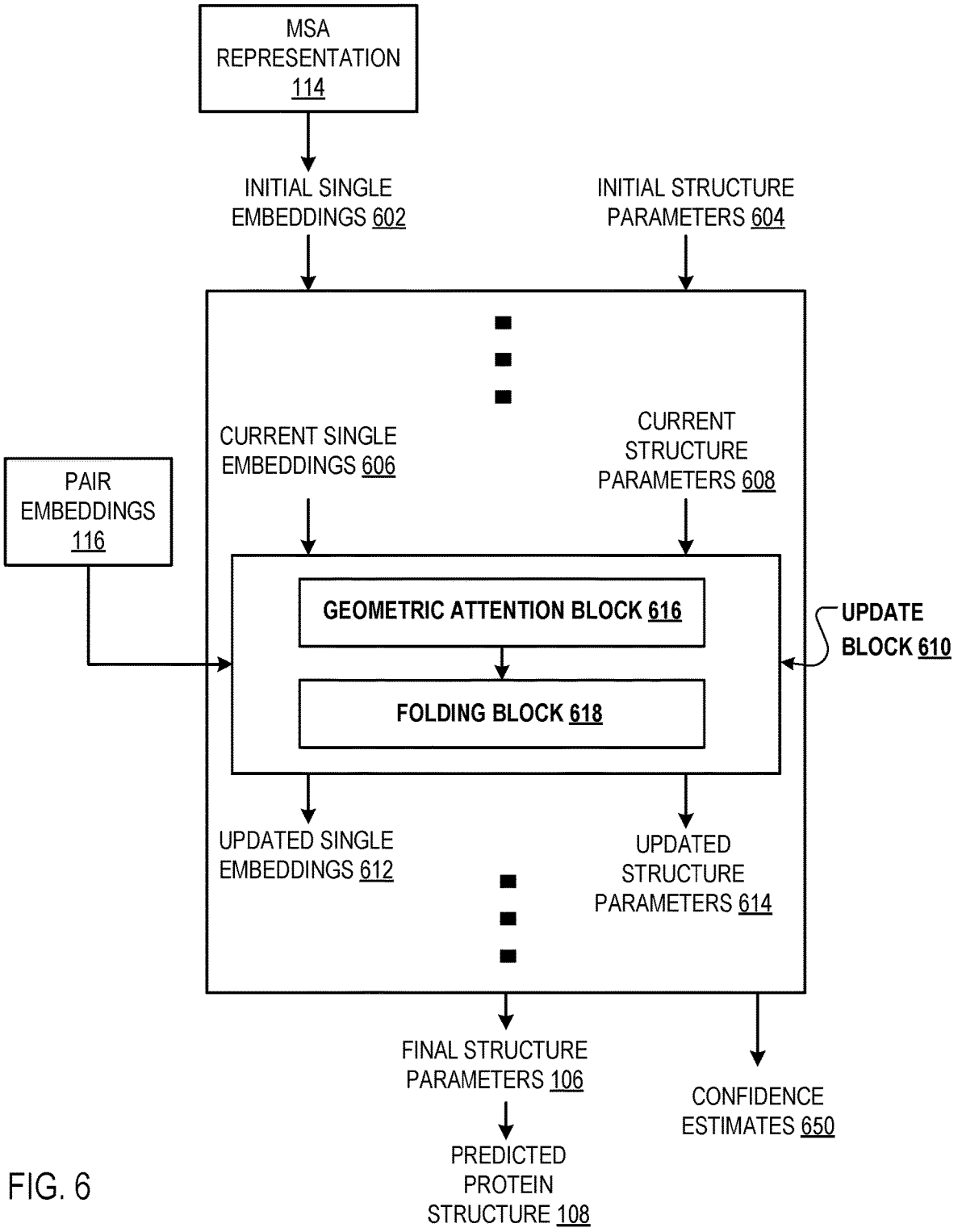
FIG. 6 shows an example architecture of a folding neural network.

FIG. 6 shows an example architecture of a main folding neural network 600 that generates a set of structure parameters 106 that define the predicted protein structure 108. For example in implementations the folding neural network 600 determines the predicted structure of the protein based on the pair embeddings by processing an input comprising a respective pair embedding 116 for each pair of amino acids in the protein to generate values of the structure parameters 106. The folding neural network 600 can be included in the protein structure prediction system 100 described with reference to FIG. 1. While the architecture shown in FIG. 6 is described with reference to the main folding neural network 600, the auxiliary folding neural network(s) 620 can also each have this same architecture, except that each auxiliary folding neural network 620 will receive input from a corresponding update block of the embedding neural network that is not the last update block in the sequence of update blocks.

In implementations, the folding neural network 600 generates structure parameters that can include: (i) location parameters, and (ii) rotation parameters, for each amino acid in the protein. As described earlier, the location parameters for an amino acid may specify a predicted 3-D spatial location of a specified atom in the amino acid in the structure of the protein. The rotation parameters for an amino acid may specify the predicted "orientation" of the amino acid in the structure of the protein. More specifically, the rotation parameters may specify a 3-D spatial rotation operation that, if applied to the coordinate system of the location parameters, causes the three "main chain" atoms in the amino acid to assume fixed positions relative to the rotated coordinate system.

In implementations the folding neural network 600 receives an input derived from the final MSA representation, the final pair embeddings, or both and generates final values of the structure parameters 106 that define a predicted structure of the protein. For example, the folding neural network 600 may receive an input that includes: (i) a respective pair embedding 116 for each pair of amino acids in the protein, (ii) initial values of a "single" embedding 602 for each amino acid in the protein, and (iii) initial values of structure parameters 604 for each amino acid in the protein. The folding neural network 600 processes the input to generate final values of the structure parameters 106 that collectively characterize the predicted structure 108 of the protein.

The protein structure prediction system 100 can provide the folding neural network 600 with the pair embeddings generated as an output of an embedding neural network, as described with reference to FIG. 1.

The protein structure prediction system 100 can generate the initial single embeddings 602 for the amino acids from the MSA representation 114, i.e., that is generated as an output of an embedding neural network, as described with reference to FIG. 1. For example, as described above, the MSA representation 114 can be represented as a 2-D array of embeddings having a number of columns equal to the number of amino acids in the protein, where each column is associated with a respective amino acid in the protein. The protein structure prediction system 100 can generate the initial single embedding for each amino acid in the protein by summing (or otherwise combining) the embeddings from the column of the MSA representation 114 that is associated with the amino acid. As another example, the protein structure prediction system 100 can generate the initial single embeddings for the amino acids in the protein by extracting the embeddings from a row of the MSA representation 114 that corresponds to the amino acid sequence of the protein whose structure is being estimated.

The protein structure prediction system 100 may generate the initial structure parameters 604 with default values, e.g., where the location parameters for each amino acid are initialized to the origin (e.g., [0,0,0] in a Cartesian coordinate system), and the rotation parameters for each amino acid are initialized to a 3×3 identity matrix.

The folding neural network 600 can generate the final structure parameters 106 by repeatedly updating the current values of the single embeddings 606 and the structure parameters 608, i.e., starting from their initial values. More specifically, the folding neural network 600 includes a sequence of update neural network blocks 610, where each update block 610 is configured to update the current single embeddings 606 (i.e., to generate updated single embeddings 612) and to update the current structure parameters

608 (i.e., to generate updated structure parameters 614). The folding neural network 600 may include other neural network layers or blocks in addition to the update blocks, e.g., that may be interleaved with the update blocks.

Each update block 610 can include: (i) a geometric attention block 616, and (ii) a folding block 618, each of which will be described in more detail next.

The geometric attention block 616 updates the current single embeddings using a "geometric" self-attention operation that explicitly reasons about the 3-D geometry of the amino acids in the structure of the protein, i.e., as defined by the structure parameters. More specifically, to update a given single embedding, the geometric attention block 616 determines a respective attention weight between the given single embedding and each of one or more selected single embeddings, where the attention weights depend on both the current single embeddings, the current structure parameters, and the pair embeddings. The geometric attention block 616 then updates the given single embedding using: (i) the attention weights, (ii) the selected single embeddings, and (iii) the current structure parameters.

To determine the attention weights, the geometric attention block 616 processes each current single embedding to generate a corresponding "symbolic query" embedding, "symbolic key" embedding, and "symbolic value" embedding. For example, the geometric attention block 616 may generate the symbolic query embedding $q_i$, symbolic key embedding $k_i$, and symbolic value embedding $v_i$ for the single embedding $h_i$ corresponding to the i-th amino acid as:

$$q_i = \text{Linear}(h_i) \tag{10}$$

$$k_i = \text{Linear}(h_i) \tag{11}$$

$$v_i = \text{Linear}(h_i) \tag{12}$$

where Linear(·) refers to linear layers having independent learned parameter values.

The geometric attention block 616 additionally processes each current single embedding to generate a corresponding "geometric query" embedding, "geometric key" embedding, and "geometric value" embedding. The geometric query, geometric key, and geometric value embeddings for each single embedding are each 3-D points that are initially generated in the local reference frame of the corresponding amino acid, and then rotated and translated to a global reference frame using the structure parameters for the amino acid. For example, the geometric attention block 616 may generate the geometry query embedding $$q_i^p,$$

geometric key embedding $$k_i^p,$$

and geometric value embedding $$v_i^p$$

for the single embedding $h_i$ corresponding to the i-th amino acid as:

$$q_i^p = R_i \cdot \text{Linear}_p(h_i) + t_i \tag{13}$$

$$k_i^p = R_i \cdot \text{Linear}_p(h_i) + t_i \tag{14}$$

$$v_i^p = R_i \cdot \text{Linear}_p(h_i) + t_i \tag{15}$$

where $\text{Linear}_p(\cdot)$ refers to linear layers having independent learned parameter values that project h i to a 3-D point (the superscript p indicates that the quantity is a 3-D point), $R_i$ denotes the rotation matrix specified by the rotation parameters for the i-th amino acid, and $t_i$ denotes the location parameters for the i-th amino acid.

To update the single embedding $h_i$ corresponding to amino acid i, the geometric attention block 616 may generate attention weights $$[a_j]_{j=1}^N,$$

where N is the total number of amino acids in the protein and $a_j$ is the attention weight between amino acid i and amino acid j, as:

$$[a_j]_{j=1}^N = \text{softmax}\left(\left[\frac{q_i \cdot k_j}{\sqrt{m}} + \alpha |q_i^p - k_j^p|_2^2 + (b_{i,j} \cdot w)\right]_{j=1}^N\right) \tag{16}$$

where $q_i$ denotes the symbolic query embedding for amino acid i, $k_j$ denotes the symbolic key embedding for amino acid j, m denotes the dimensionality of $q_i$ and $k_j$, $\alpha$ denotes a learned parameter, $$q_i^p$$

denotes the geometric query embedding for amino acid i, $$k_j^p$$

denotes the geometry key embedding for amino acid j, $|\cdot|_2$ is an $L_2$ norm, and $b_{i,j}$ is the pair embedding 116 corresponding to the pair of amino acids that includes amino acid i and amino acid j, and w is a learned weight vector (or some other learned projection operation).

Generally, the pair embedding for a pair of amino acids implicitly encodes information relating the relationship between the amino acids in the pair, e.g., the distance between the amino acids in the pair. By determining the attention weight between amino acid i and amino acid j based in part on the pair embedding for amino acids i and j, the folding neural network 600 enriches the attention weights with the information from the pair embedding and thereby improves the accuracy of the predicted folding structure.

In some implementations, the geometric attention block 616 generate multiple sets of geometric query embeddings, geometric key embeddings, and geometric value embeddings, and uses each generated set of geometric embeddings in determining the attention weights.

After generating the attention weights for the single embedding $h_i$ corresponding to amino acid i, the geometric attention block 616 uses the attention weights to update the single embedding $h_i$. In particular, the geometric attention block 616 uses the attention weights to generate a "symbolic return" embedding and a "geometric return" embedding, and then updates the single embedding using the symbolic return embedding and the geometric return embedding. The geometric attention block 124 may generate the symbolic return embedding $o_i$ for amino acid i, e.g., as:

$$o_i = \sum_j a_j v_j \qquad (17)$$

where $$[a_j]_{j=1}^N$$

denote the attention weights (e.g., defined with reference to equation (16)) and each $v_j$ denotes the symbolic value embedding for amino acid j. The geometric attention block 616 may generate the geometric return embedding $$o_i^p$$

for amino acid i, e.g., as:

$$o_i^p = R_i^{-1} \cdot \left( \sum_j a_j v_j^p - t_i \right) \qquad (18)$$

where the geometric return embedding $$o_i^p$$

is a 3-D point, $$[a_j]_{j=1}^N$$

denote the attention weights (e.g., defined with reference to equation (16)), $$R_i^{-1}$$

is inverse of the rotation matrix specified by the rotation parameters for amino acid i, and $t_i$ are the location parameters for amino acid i. It can be appreciated that the geometric return embedding is initially generated in the global reference frame, and then rotated and translated to the local reference frame of the corresponding amino acid.

The geometric attention block 616 may update the single embedding $h_i$ for amino acid i using the corresponding symbolic return embedding $o_i$ (e.g., generated in accordance with equation (17)) and geometric return embedding $$o_i^p$$

(e.g., generated in accordance with equation (18)), e.g., as:

$$h_i^{next} = \text{LayerNorm}\left(h_i + \text{Linear}\left(o_i, o_i^p, |o_i^p|\right)\right) \qquad (19)$$

where $$h_i^{next}$$

is the updated single embedding for amino acid i, |·| is a norm, e.g., an $L_2$ norm, and LayerNorm(·) denotes a layer normalization operation, e.g., as described with reference to: J. L. Ba, J. R. Kiros, G. E. Hinton, "Layer Normalization," arXiv:1607.06450 (2016).

Updating the single embeddings 606 of the amino acids using concrete 3-D geometric embeddings, e.g., as described with reference to equations (13)-(15), enables the geometric attention block 616 to reason about 3-D geometry in updating the single embeddings. Moreover, each update block updates the single embeddings and the structure parameters in a manner that is invariant to rotations and translations of the overall protein structure. For example, applying the same global rotation and translation operation to the initial structure parameters provided to the folding neural network 600 would cause the folding neural network 600 to generate a predicted structure that is globally rotated and translated in the same way, but otherwise the same. Therefore, global rotation and translation operations applied to the initial structure parameters would not affect the accuracy of the predicted protein structure generated by the folding neural network 600 starting from the initial structure parameters. The rotational and translational invariance of the representations generated by the folding neural network 600 facilitates training, e.g., because the folding neural network 600 automatically learns to generalize across all rotations and translations of protein structures.

The updated single embeddings for the amino acids may be further transformed by one or more additional neural network layers in the geometric attention block 616, e.g., linear neural network layers, before being provided to the folding block 618.

After the geometric attention block 616 updates the current single embeddings 606 for the amino acids, the folding block 618 updates the current structure parameters 608 using the updated single embeddings 612. For example, the folding block 618 may update the current location parameters $t_i$ for amino acid i as:

$$t_i^{next} = t_i + \text{Linear}(h_i^{next}) \qquad (20)$$

where $$t_i^{next}$$

are the updated location parameters, Linear(·) denotes a linear neural network layer, and $$h_i^{next}$$

denotes the updated single embedding for amino acid i. In another example, the rotation parameters $R_i$ for amino acid i may specify a rotation matrix, and the folding block 618 may update the current rotation parameters $R_i$ as:

$$w_i = \text{Linear}(h_i^{next}) \tag{21}$$

$$R_i^{next} = R_i \cdot QuaternionToRotation(1 + w_i) \tag{22}$$

where $w_i$ is a three-dimensional vector, Linear(·) is a linear neural network layer, $$h_i^{next}$$

is the updated single embedding for amino acid i, $1+w_i$ denotes a quaternion with real part 1 and imaginary part $w_i$, and QuaternionToRotation(·) denotes an operation that transforms a quaternion into an equivalent 3×3 rotation matrix. Updating the rotation parameters using equations (21)-(22) ensures that the updated rotation parameters define a valid rotation matrix, e.g., an orthonormal matrix with determinant one.

The folding neural network 600 may provide the updated structure parameters generated by the final update block 610 as the final structure parameters 106 that define the predicted protein structure 108. The folding neural network 600 may include any appropriate number of update blocks, e.g., 5 update blocks, 25 update blocks, or 125 update blocks. Optionally, each of the update blocks of the folding neural network may share a single set of parameter values that are jointly updated during training of the folding neural network. Sharing parameter values between the update blocks 610 reduces the number of trainable parameters of the folding neural network and may therefore facilitate effective training of the folding neural network, e.g., by stabilizing the training and reducing the likelihood of overfitting.

During training, a training engine can train the parameters of the structure prediction system, including the parameters of the folding neural network 600, based on a structure loss that evaluates the accuracy of the final structure parameters 106, as described above. In some implementations, the training engine can further evaluate an auxiliary structure loss for one or more of the update blocks 610 that precede the final update block (i.e., that produces the final structure parameters). The auxiliary structure loss for an update block evaluates the accuracy of the updated structure parameters generated by the update block.

Optionally, during training, the training engine can apply a "stop gradient" operation to prevent gradients from back-propagating through certain neural network parameters of each update block, e.g., the neural network parameters used to compute the updated rotation parameters (as described in equations (21)-(22)). Applying these stop gradient operations can improve the numerical stability of the gradients computed during training.

Generally, a similarity between the predicted protein structure 108 generated by the folding neural network 600 and the corresponding ground truth protein structure can be measured, e.g., by a similarity measure that assigns a respective accuracy score to each of multiple atoms in the predicted protein structure. For example, the similarity measure can assign a respective accuracy score to each carbon alpha atom in the predicted protein structure. The accuracy score for an atom in the predicted protein structure can characterize how closely the position of the atom in the predicted protein structure conforms with the actual position of the atom in the ground truth protein structure. An example of a similarity measure that can compare the predicted protein structure to the ground truth protein structure to generate accuracy scores for the atoms in predicted protein structure is the 1DDT similarity measure described with reference to: V. Mariani et al., "1DDT: a local superposition-free score for comparing protein structures and models using distance difference tests," Bioinformatics, 2013 Nov. 1; 29(21) 2722-2728.

The folding neural network 600 can be configured to generate a respective confidence estimate 650 for each of one or more atoms in the predicted protein structure 108. The confidence estimate 650 for an atom in the predicted protein structure characterizes the predicted accuracy score (e.g., 1DDT accuracy score) for the atom in the predicted protein structure, i.e., that would be generated by a similarity measure that compares the predicted protein structure to the (potentially unknown) ground truth protein structure. In one example, the confidence estimate 650 for an atom in the predicted protein structure can define a discrete probability distribution over a set of intervals that form a partition of a range of possible values for the accuracy score for the atom. The discrete probability distribution can associate a respective probability with each of the intervals that defines the likelihood that the actual accuracy score is included in the interval. For example, range of possible values of the accuracy score may be [0, 100], and the confidence estimate 650 may define a probability distribution over the set of intervals {[0, 2), [2, 4), . . . , [98,100]}. In another example, the confidence estimate 650 for an atom in the predicted protein structure can be a numerical value, i.e., that directly predicts the accuracy score for the atom.

In some implementations, the folding neural network 600 generates a respective confidence estimate 650 for a specified atom (e.g., the alpha carbon atom) in each amino acid of the protein. The folding neural network 600 can generate the confidence estimate 650 for the specified atom in an amino acid in the protein, e.g., by processing the updated single embedding for the amino acid that is generated by the last update block in the folding neural network using one or more neural network layers, e.g., fully-connected layers.

The structure prediction system can generate a respective confidence score corresponding to each amino acid in the protein based on the confidence estimates 650 for the atoms in the predicted protein structure. For example, the structure prediction system can generate a confidence score for an amino acid as the expected value of a probability distribution over possible values of the accuracy score for the alpha carbon atom in the amino acid.

The structure prediction system can generate a confidence score for the entire predicted structure, e.g., as an average of the confidence scores for the amino acids in the protein.

During training of the structure prediction system, a training engine can adjust the parameter values of the structure prediction system by backpropagating gradients of an auxiliary loss that measures an error between: (i) confidence estimates generated by the folding neural network 600, and (ii) accuracy scores generated by comparing the predicted protein structure to the ground truth protein structure. The error may be, e.g., a cross-entropy error.

Confidence estimates generated by structure prediction systems can be used in a variety of ways. For example, confidence estimates for atoms in the predicted protein structure can indicate which parts of the structure have been reliably estimated are therefore suitable for further downstream processing or analysis. As another example, per-protein confidence scores can be used to rank a set of predictions for the structure of a protein, e.g., that have been generated by the same structure prediction system by processing different inputs characterizing the same protein, or that have been generated by different structure prediction systems.

The location and rotation parameters specified by the structure parameters 106 can define the spatial locations (e.g., in [x, y, z] Cartesian coordinates) of the main chain atoms in the amino acids of the protein. However, the structure parameters 106 do not necessarily define the spatial locations of the remaining atoms in the amino acids of the protein, e.g., the atoms in the side chains of the amino acids. In particular, the spatial locations of the remaining atoms in an amino acid depend on the values of the torsion angles between the bonds in the amino acid, e.g., the omega-angle, the phi-angle, the psi-angle, the chi1-angle, the chi2-angle, the chi3-angle, and the chi4 angle, as illustrated with reference to FIG. 7.

Optionally, one or more of the update blocks 610 of the folding neural network 600 can generate an output that defines a respective predicted spatial location for each atom in each amino acid of the protein. To generate the predicted spatial locations for the atoms in an amino acid, the update block can process the updated single embedding for the amino acid using one or more neural network layers to generate predicted values of the torsion angles of the bonds between the atoms in the amino acid. The neural network layers may be, e.g., fully-connected neural network layers embedded with residual connections. Each torsion angle may be represented, e.g., as a 2-D vector.

The update block can determine the spatial locations of the atoms in an amino acid based on: (i) the values of the torsion angles for the amino acid, and (ii) the updated structure parameters (e.g., location and rotation parameters) for the amino acid. For example, the update block can process the torsion angles in accordance with a predefined function to generate the spatial locations of the atoms in the amino acid in a local reference frame of the amino acid. The update block can generate the spatial locations of the atoms in the amino acid in a global reference frame (i.e., that is common to all the amino acids in the protein) by rotating and translating the spatial locations of the atoms in accordance with the updated structure parameters for the amino acid. For example, the update block can determine the spatial location of an atom in the global reference frame by applying the rotation operation defined by the updated rotation parameters to the spatial location of the atom in the local reference frame to generate a rotated spatial location, and then apply the translation operation defined by the updated location parameters to the rotated spatial location.

In some implementations, alternatively to or in combination with outputting the final structure parameters, the folding neural network 600 outputs the predicted spatial locations of the atoms in the amino acids of the protein that are generated by the final update block.

The folding neural network 600 described with reference to FIG. 6 is characterized herein as receiving an input that is based on an MSA representation 114 and pair embeddings 116 that are generated by an embedding neural network, e.g., as described with reference to FIG. 2. In general, however, the inputs to the folding neural network (e.g., the single embeddings 602 and the pair embeddings 116) can be generated using any appropriate technique. Moreover, various aspects of the operations performed by the folding neural network (e.g., predicting spatial locations for the atoms in each amino acid of the protein) can be performed by other folding neural networks, e.g., with different architectures that receive different inputs.

Figure 7:
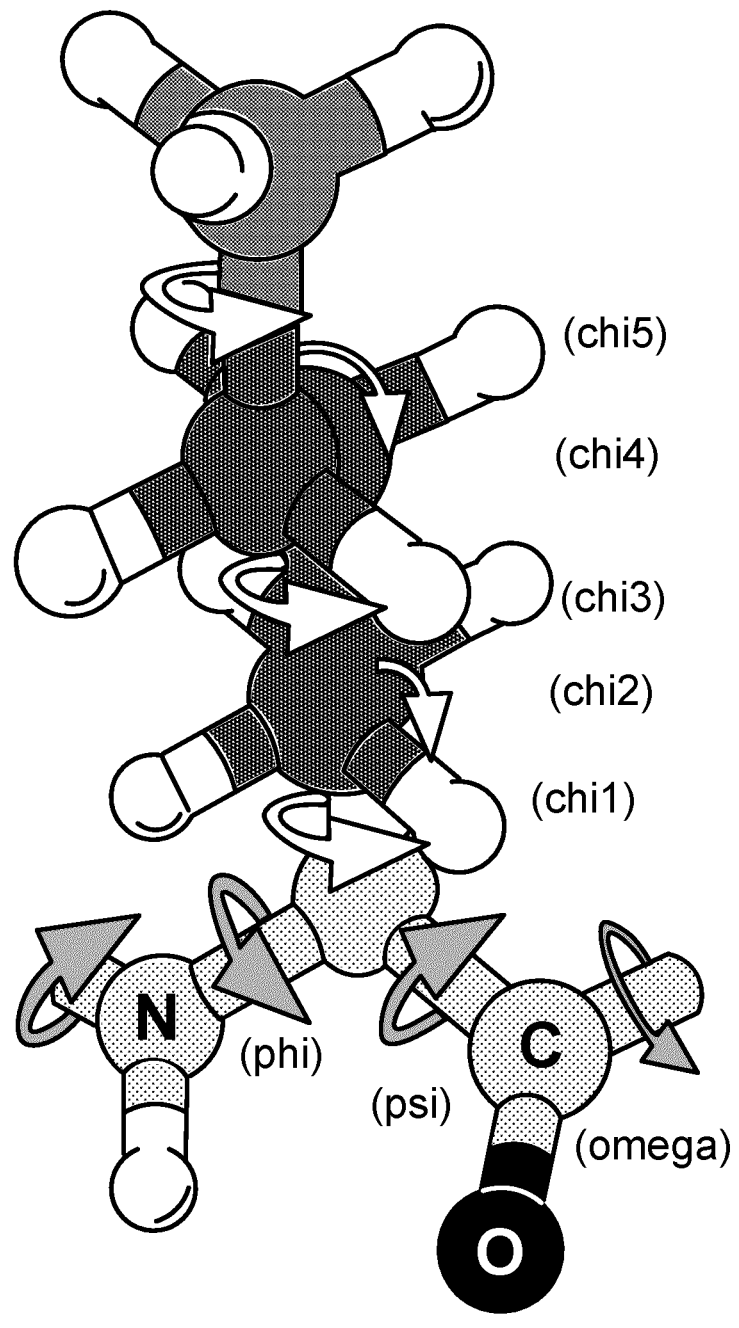
FIG. 7 illustrates the torsion angles between the bonds in the amino acid.

FIG. 7 illustrates the torsion angles between the bonds in the amino acid, e.g., the omega-angle, the phi-angle, the psi-angle, the chi1-angle, the chi2-angle, the chi3-angle, the chi4 angle, and the chi5 angle.

Figure 8:
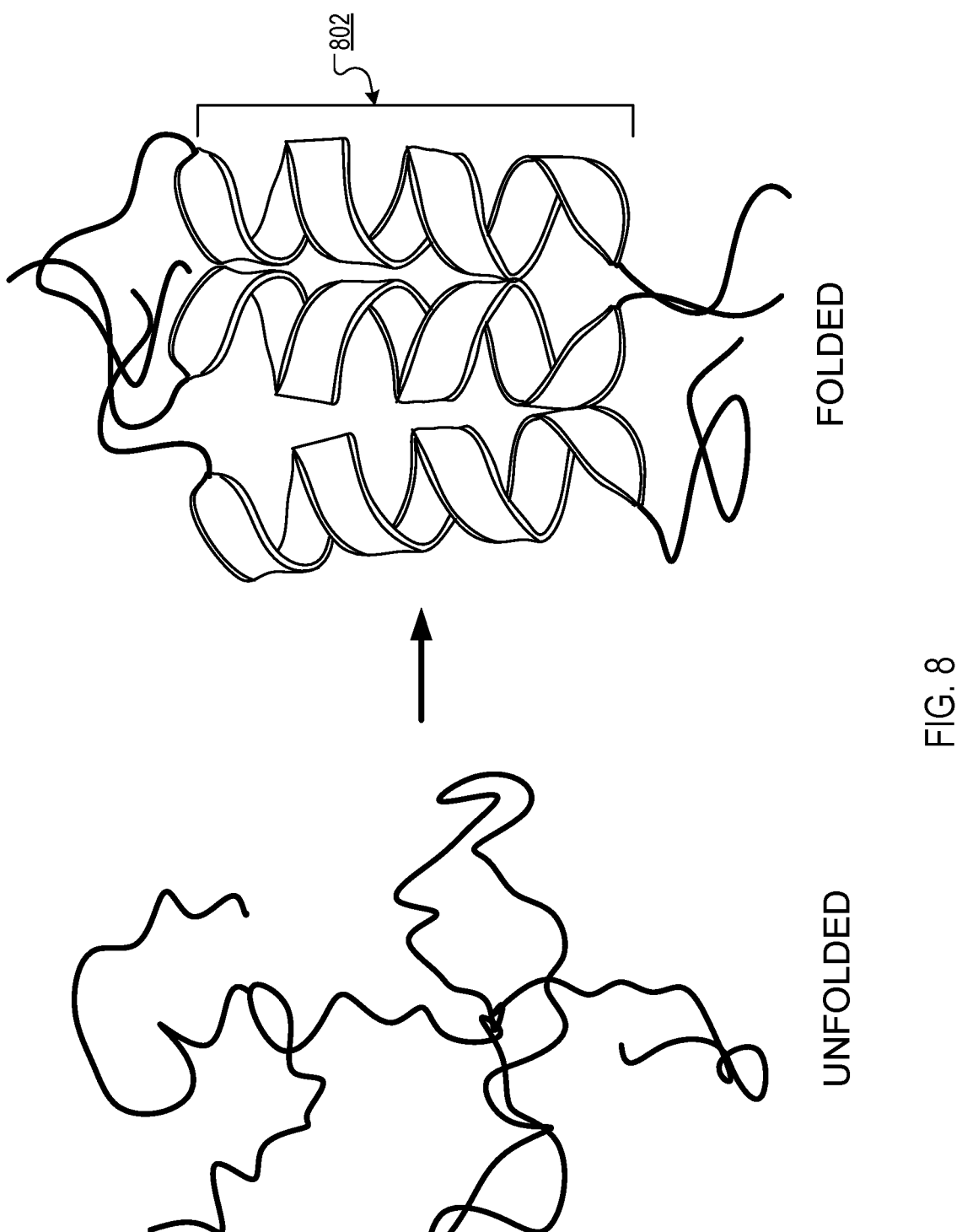
FIG. 8 is an illustration of an unfolded protein and a folded protein.

FIG. 8 is an illustration of an unfolded protein and a folded protein. The unfolded protein is a random coil of amino acids. The unfolded protein undergoes protein folding and folds into a 3D configuration. Protein structures often include stable local folding patterns such alpha helices (e.g., as depicted by 802) and beta sheets.

Figure 9:
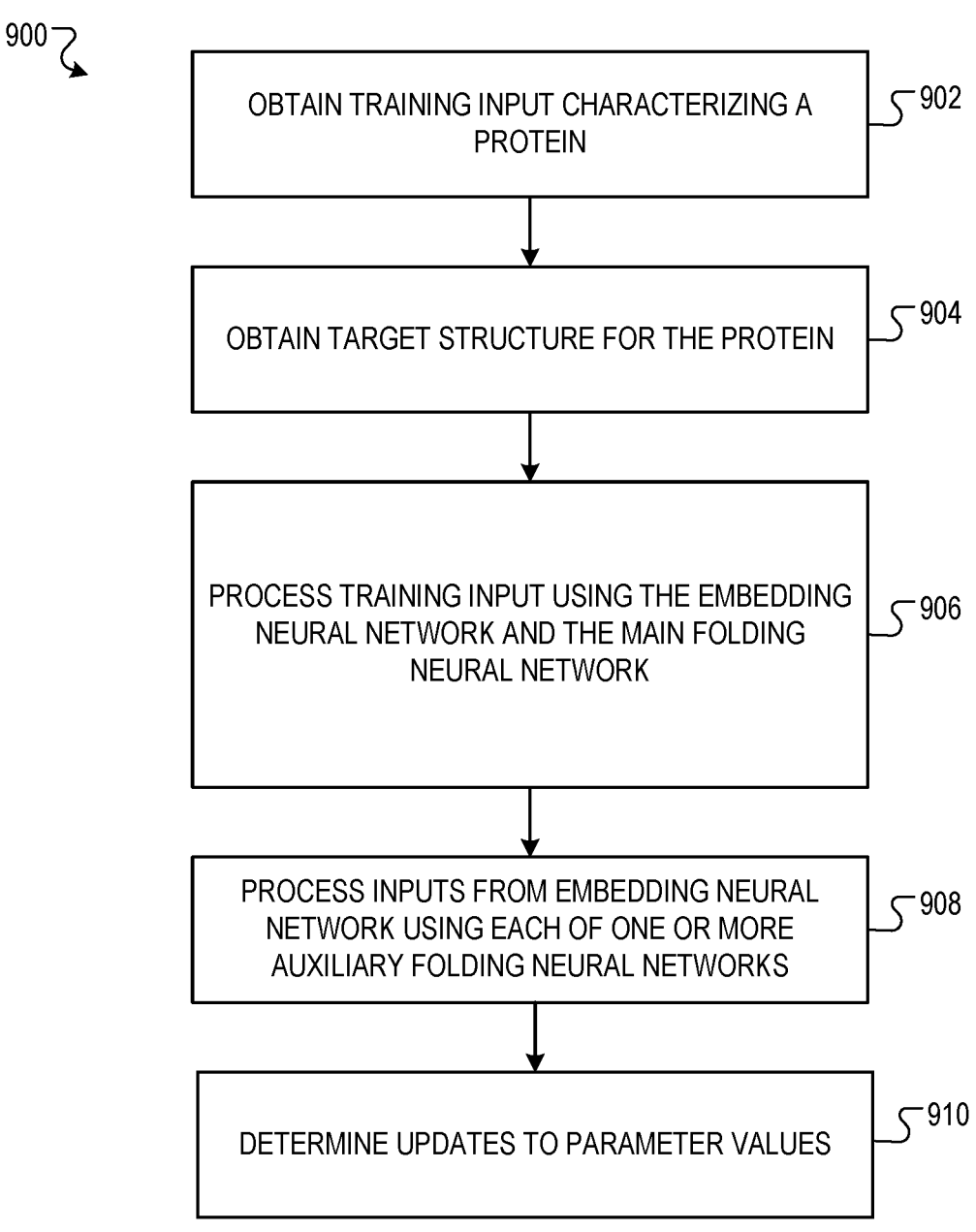
FIG. 9 is a flow diagram of an example process for training a structure prediction neural network.

FIG. 9 is a flow diagram of an example process 900 for training a structure prediction neural network that includes an embedding neural network and a main folding neural network. For convenience, the process 900 will be described as being performed by a system of one or more computers located in one or more locations. For example, a protein structure prediction system, e.g., the protein structure prediction system 100 of FIG. 1, appropriately programmed in accordance with this specification, can perform the process 900.

The system obtains a training input that includes data characterizing a given protein (step 902). For example, the data can include (i) an initial multiple sequence alignment (MSA) representation that represents a respective MSA corresponding to each chain in the protein and (ii) a respective initial pair embedding for each pair of amino acids in the protein.

The system obtains data specifying a target protein structure that should be generated by the system 100 by processing the training input (step 904).

The system processes the training input using the embedding neural network and the main folding neural network, e.g., as described above, to generate a main structure prediction (step 906).

For each of one or more auxiliary folding neural networks, the system processes an input that includes the updated pair embeddings generated by corresponding one of the "hidden" update blocks in the embedding neural network to generate an auxiliary structure prediction (step 908). A hidden update block is an update block that is not the last update block in the sequence. In implementations in which the auxiliary structure predictions are fed back into the embedding neural network, the system performs step 908 while performing step 906, i.e., because the output of the embedding neural network depends on the auxiliary structure prediction(s) generated by the auxiliary folding neural network(s). In implementations in which the auxiliary structure predictions are not fed back into the embedding neural network, the system can either perform step 908 while performing step 906 or after step 906 has been performed, i.e., after the main structure prediction has been generated.

The system computes gradients (step 910) with respect to each of the parameters of the neural networks of a loss function that includes at least (a) a main structure loss that characterizes a similarity between (i) a predicted protein structure defined by the main structure prediction generated by the main folding neural network, and (ii) the target protein structure that should have been generated by the system and (b) respective auxiliary structure losses for each of the auxiliary neural network(s). The auxiliary structure loss for a given auxiliary neural network characterizes the similarity between (i) a predicted protein structure defined by the auxiliary structure prediction generated by the given auxiliary folding neural network, and (ii) the target protein structure that should have been generated by the system.

Once a threshold condition has been satisfied, e.g., gradients for an entire batch of training inputs have been computed, the system can then compute an update to the parameter values of the embedding neural network, the main folding neural network, and the auxiliary folding neural network(s) from the gradients in accordance with the update rule of the optimizer being used for the training, e.g., Adam, rmsProp, or SGD. The system can then apply the updates to the current values of the parameters, i.e., subtract the updates from or add the updates to the current values.

After training, the system can perform the process 900 without performing steps 904, 910 and, in implementations in which outputs from the auxiliary folding networks are not fed back into the embedding neural network, step 908, and then provide the main structure prediction or other information specifying the structure defined by the main structure prediction as the output of the system for the protein characterized by the input.

Figure 10:
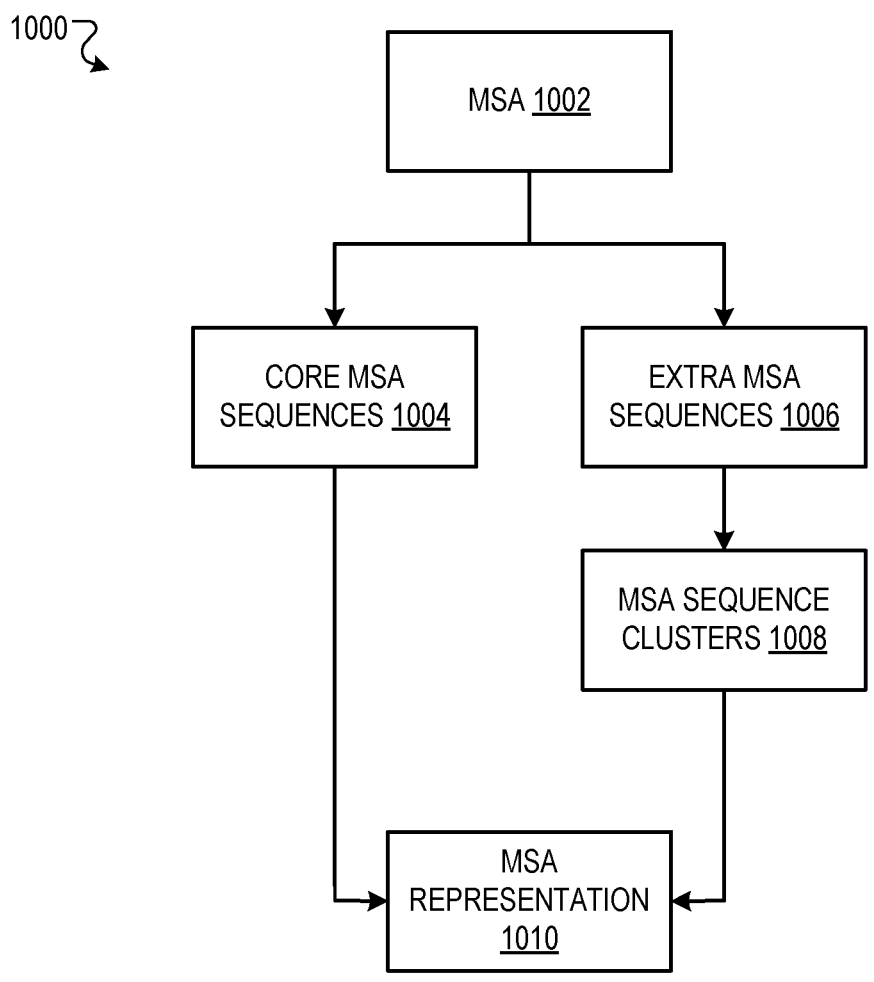
FIG. 10 shows an example process for generating a MSA representation for an amino acid chain in a protein.

FIG. 10 shows an example process 1000 for generating a MSA representation 1010 for an amino acid chain in the protein. The protein structure prediction system 100, described with reference to FIG. 1, can implement the operations of the process 1000.

To generate the MSA representation 1010 for the amino acid chain in the protein, the system 100 obtains a MSA 1002 for the protein that may include, e.g., thousands of MSA sequences.

The system 100 divides the set of MSA sequences into a set of "core" MSA sequences 1004 and a set of "extra" MSA sequences 1006. The set of core MSA sequences can be smaller (e.g., by an order of magnitude) than the set of extra MSA sequences 1006. The system 100 can divide the set of MSA sequences into core MSA sequences 1004 and extra MSA sequences 1006, e.g., by randomly selecting a predetermined number of the MSA sequences as core MSA sequences, and identifying the remaining MSA sequences as extra MSA sequences 1006.

For each extra MSA sequence 1006, the system 100 can determine a respective similarity measure (e.g., based on a Hamming distance) between the extra MSA sequence and each core MSA sequence 1004. The system 100 can then associate each extra MSA sequence 1006 with the corresponding core MSA sequence 1004 to which the extra MSA sequence 1006 is most similar (i.e., according to the similarity measure). The set of extra MSA sequences 1006 associated with a core MSA sequence 1004 can be referred to as a "MSA sequence cluster" 1008. That is, the system 100 determines a respective MSA sequence cluster 1008 corresponding to each core MSA sequence 1004, where the MSA sequence cluster 1008 corresponding to a core MSA sequence 1004 includes the set of extra MSA sequences 1006 that are most similar to the core MSA sequence 1004.

The system 100 can generate the MSA representation for the amino acid chain in the protein based on the core MSA sequences and the MSA sequence clusters 1008. The MSA representation 1010 can be represented by an M×N array of embeddings, where M is the number of core MSA sequences (i.e., such that each core MSA sequence is associated with a respective row of the MSA representation), and N is the number of amino acids in the amino acid chain. The embeddings in the MSA representation can be indexed by $(i,j) \in \{ (i,j): i=1, \ldots, M, j=1, \ldots, N \}$.

To generate the embedding at position (i,j) in the MSA representation 1010, the system 100 can obtain an embedding (e.g., a one-hot embedding) defining the identity of the amino acid at position j in core MSA sequence i. The system 100 can also determine a probability distribution over the set of possible amino acids based on the relative frequency of occurrence of each possible amino acid at position j in the extra MSA sequences 1006 in the MSA sequence cluster 1008 corresponding to core MSA sequence i. The system 100 can then determine the embedding at position (i,j) in the MSA representation by combining (e.g., concatenating): (i) the embedding defining the identity of the amino acid at position j in core MSA sequence i, and (ii) the probability distribution over possible amino acids corresponding to position j in core MSA sequence i.

In some cases, the (ground truth) protein structure may be known for one or more of the core MSA sequences. In particular, for one or more of the core MSA sequences, the values of the torsion angles between the bonds in the amino acids in the core MSA sequence (e.g., the omega-angle, the phi-angle, the psi-angle, etc.) may be known. If the values of the torsion angles for the amino acids in core MSA sequence i are known, then the system 100 can generate the embedding at position (i,j) in the MSA representation based at least in part on the values of the torsion angles for amino acid j in core MSA sequence i. For example, the system can generate an embedding of the values of the torsion angles using one or more neural network layers, and the concatenate the embedding of the values of the torsion angles to the embedding at position (i,j) in the MSA representation.

Figure 11:
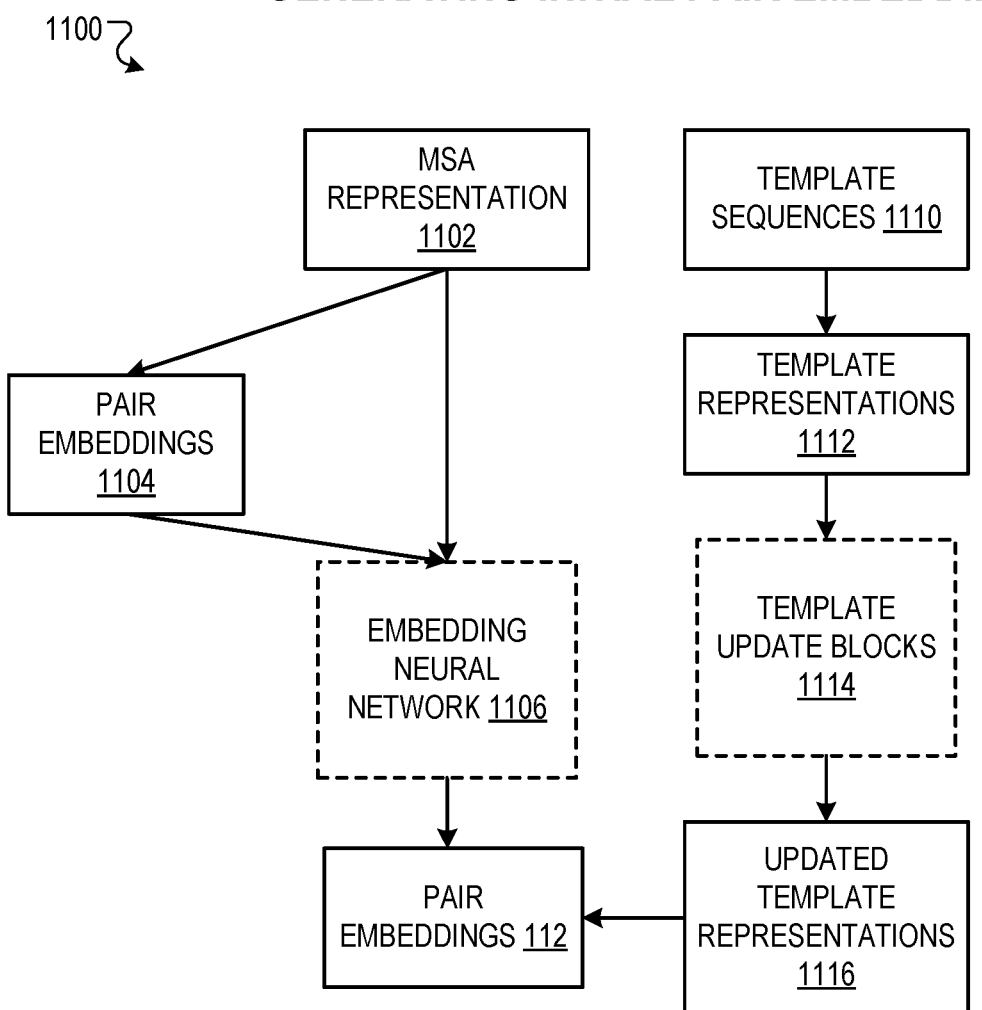
FIG. 11 shows an example process for generating a respective pair embedding for each pair of amino acids in a protein.

FIG. 11 shows an example process 1100 for generating (initializing) a respective pair embedding 112 for each pair of amino acids in the protein. The protein structure prediction system 100, described with reference to FIG. 1, can implement the operations of the process 1100.

The system 100 can generate the pair embeddings 112 using an MSA representation 1102 of the protein. Generating a MSA representation for the protein is described in more detail with reference to FIG. 1 and FIG. 10. The system 100 can generate the MSA representation 1102 for the protein based on a respective MSA representation for each amino acid chain in the protein. To generate the MSA representation for an amino acid chain in the protein, the system 100 can use more MSA sequences (e.g., by an order of magnitude) than were used to generate the MSA representation 110 described with reference to FIG. 1. Therefore, the MSA representation 1102 used by the system 100 to generate the pair embeddings 112 may have more rows (e.g., by an order of magnitude) than the MSA representation 110 described with reference to FIG. 1. In some implementations, the system 100 can use the extra MSA sequences 1006 described with reference to FIG. 10 to generate the MSA representation 1102.

After generating the MSA representation 1102, the system 100 processes the MSA representation 1102 to generate pair embeddings 1104 from the MSA representation 1102, e.g., by applying an outer product mean operation to the MSA representation 1102, and identifying the pair embeddings 1104 as the result of the outer product mean operation.

The system 100 processes the MSA representation 1102 and the pair embeddings 1104 using an embedding neural network 1106. The embedding neural network 1106 can update the MSA representation 1102 and the pair embeddings 1104 by sharing information between the MSA representation 1102 and the pair embeddings 1104. More specifically, the embedding neural network 1106 can alternate between updating the MSA representation 1102 based on the pair embeddings 1104, and updating the pair embeddings 1104 based on the MSA representation 1102.

The embedding neural network 1106 can have an architecture based on the embedding neural network architecture described with reference to FIGS. 2-5, i.e., that updates the pair embeddings 1104 and the MSA representation 1102 using row-wise and column-wise self-attention blocks.

In some implementations, the embedding neural network 1106 can update the embeddings in each column of the MSA representation 1102 using a column-wise "global" self-attention operation. More specifically, the embedding neural network 1106 can provide the embeddings in each column of the MSA representation to a column-wise global self-attention block to generate updated embeddings for each column of the current MSA representation. To implement global column-wise self-attention, the self-attention block can generate a respective query embedding for each embedding in a column, and then average the query embeddings to generate a single "global" query embedding for the column. The column-wise self-attention block then uses the single global query embedding to perform the self-attention operation, which can reduce the complexity of the self-attention operation from quadratic (i.e., in the number of embeddings per column) to linear. Using a global self-attention operation can reduce the computational complexity of the column-wise self-attention operation to enable the column-wise self-attention operation to be performed on columns of the MSA representation 1102 that include large numbers (e.g., thousands) of embeddings.

After updating the pair embeddings 1104 and the MSA representation 1102 using the embedding neural network 1106, the system 100 can identify the pair embeddings 112 as the updated pair embeddings generated by the embedding neural network 1106. The system 100 can discard the updated MSA representation generated by the embedding neural network 1106, or use it in any appropriate way.

As part of generating the pair embeddings 112, the system 100 can include relative position encoding information in the respective pair embedding corresponding to each pair of amino acids in the protein. The system can include the relative position encoding information for a pair of amino acids that are included in the same amino acid chain in the corresponding pair embedding by: computing the signed difference representing the number of amino acids separating the pair of amino acids in the amino acid chain, clipping the result to a predefined interval, representing the clipped value using a one-hot encoding vector, applying a linear transformation to the one-hot encoding vector, and adding the result of the linear transformation to the corresponding pair embedding. The system can include the relative position encoding information for a pair of amino acids that are not included in the same amino acid chain in the corresponding pair embedding by adding a default encoding vector to the corresponding pair embedding which indicates that the pair of amino acids are not included in the same amino acid chain.

The system 100 can also generate the pair embeddings 112 based at least in part on a set of one or more template sequences 1110. Each template sequence 1110 is an MSA sequence for an amino acid chain in the protein where the folded structure of the template sequence 1110 is known, e.g., from physical experiments.

The system 100 can generate a respective template representation 1112 of each template sequence 1110. A template representation 1112 of a template sequence 1110 includes a respective embedding corresponding to each pair of amino acids in the template sequence, e.g., such that a template representation 1112 of a template sequence of length n (i.e., with n amino acids) can be represented as an n×n array of embeddings. The system 100 generate the embedding at position (i,j) in the template representation 1112 of a template sequence 1110 based on, e.g.: (i) respective embeddings (e.g., one-hot embeddings) representing the identities of the amino acid at position i and position j in the template sequence, (ii) a unit vector defined by the difference in spatial positions of the respective carbon alpha atoms in the amino acids at position i and j in the template sequence, i.e., in the folded structure of the template sequence, where the unit vector is computed in the frame of reference of amino acid i or amino acid j, and (iii) a discretized/binned representation of the distance between the spatial positions of the respective carbon alpha atoms in the amino acids at position i and j in the template sequence.

The system 100 can process each template representation using a sequence of one or more template update blocks 1114 to generate a respective updated template representation 1116 corresponding to each template sequence 1110. The template update blocks can include, e.g., row-wise self-attention blocks (e.g., that update the embeddings in each row of the template representations), column-wise self-attention blocks (e.g., that update the embeddings in each column of the template representations), and transition blocks (e.g., that apply one or more neural network layers to each of the embeddings in the template representations).

After generating the updated template representations 1116, the system 100 uses the updated template representations 1116 to update the pair embeddings 112. For example, the system 100 can update the respective pair embedding 112 at each position (i,j) using "cross-attention" over the embeddings at the corresponding (i,j) positions of the updated template representations 1116. In a cross-attention operation to update the pair embedding 112 at position (i,j), the query embedding is generated from the pair embedding at position (i,j), and the key and value embeddings are generated from the embeddings at the corresponding (i,j) positions of the updated template representations 1116.

Updating the pair embeddings 112 using the template sequences 1110 enables the system 100 to enrich the pair embeddings with information characterizing the protein structures of the evolutionarily related template sequences 1110, thereby enhancing the information content of the pair embeddings 112, and improving the accuracy of protein structures predicted using the pair embeddings.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, specialpurpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method of training a structure prediction neural network, wherein the structure prediction neural network comprises (i) an embedding neural network having a plurality of embedding parameters and that is configured to receive a network input characterizing a protein and to process the network input in accordance with the embedding parameters to generate an embedding output for the network input and (ii) a main folding neural network having a plurality of main folding parameters and that is configured to receive the embedding output and to process the embedding output in accordance with the main folding parameters to generate a main structure prediction that defines a predicted structure of the protein, the method comprising:

obtaining a training network input characterizing a training protein and data specifying a target protein structure for the training protein;

processing the training network input using the embedding neural network and in accordance with current values of the embedding parameters to generate a training embedding output for the training network input;

processing the training embedding output using the main folding neural network and in accordance with current values of the main folding parameters to generate a main structure prediction that defines a main predicted structure of the training protein;

for each auxiliary folding neural network in a set of one or more auxiliary folding neural networks that each have a respective plurality of auxiliary folding parameters, processing at least a corresponding intermediate output of the embedding neural network using the auxiliary folding neural network and in accordance with current values of the respective auxiliary folding parameters of the auxiliary folding neural network to generate an auxiliary structure prediction that defines an auxiliary predicted structure of the training protein;

determining a gradient of an objective function that includes:

a main structure loss term that characterizes a similarity between: (i) the main predicted structure defined by the main structure prediction, and (ii) the target protein structure for the training protein; and a respective auxiliary structure loss term for each of the auxiliary folding neural networks that characterizes a similarity between: (i) the auxiliary predicted structure defined by the auxiliary structure prediction generated by the auxiliary structure prediction neural network, and (ii) the target protein structure for the training protein; and updating the current values of the embedding network parameters, the main folding parameters, and the respective auxiliary folding parameters of the one or more auxiliary folding neural networks based on the gradient.

2. The method of claim 1, wherein each auxiliary folding neural network has a same neural network architecture as the main folding neural network.

3. The method of claim 2, wherein the set of one or more auxiliary folding neural networks comprises a plurality of auxiliary folding neural networks and wherein the objective function constrains the auxiliary folding neural networks to share parameter values.

4. The method of claim 2, wherein the objective function constrains the auxiliary folding neural networks and the main folding neural network to share parameter values.

5. The method of claim 1, wherein:

the network input comprises a respective initial pair embedding for each pair of amino acids in the protein, the embedding neural network comprises a sequence of update blocks, wherein each update block performs operations comprising:

receiving a block input comprising a respective current pair embedding for each pair of amino acids in the protein; and updating the respective current pair embeddings for each pair of amino acids in the protein to generate a respective updated pair embedding for each pair of amino acids in the protein, and the embedding output comprises at least the updated pair embeddings generated by a last update block in the sequence.

6. The method of claim 5, wherein each auxiliary folding neural network corresponds to a different one of the update blocks in the sequence that is not the last update block in the sequence, and wherein each auxiliary folding neural network is configured to receive as input at least the updated pair embeddings generated by the corresponding update block.

7. The method of claim 6, wherein:

the network input further comprises an initial multiple sequence alignment (MSA) embedding that represents a respective multiple sequence alignment corresponding to each chain in the protein, the block input to each of the update blocks further comprises a current MSA embedding; and the operations performed by each update block further comprise:

updating the current MSA embedding to generate an updated MSA embedding.

8. The method of claim 7, wherein the input for each auxiliary folding neural network further comprises the updated MSA embedding generated by the corresponding update block.

9. The method of claim 7, wherein each auxiliary folding neural network is configured to:

generate, from the auxiliary structure prediction generated by the auxiliary folding neural network, a transformed structure prediction that has a same dimensionality as the updated pair embeddings;

combine the transformed structure prediction with the updated pair embeddings to generate further updated pair embeddings; and provide the further updated pair embeddings as input to an update block that follows the current update block in the sequence.

10. The method of claim 9, wherein:

the auxiliary folding prediction comprises structure parameters that specify, for each amino acid, a predicted 3-D spatial location of a specified atom in the amino acid in the structure of the protein; and generating the transformed structure prediction comprises:

generating, from the predicted 3-D spatial locations for the amino acids specified by the structure parameters, a distance map that characterizes, for each pair of amino acids in the protein, a respective estimated distance between the pair of amino acids in the structure of the protein; and generating, from the distance map, a transformed distance map that has a same dimensionality as the updated pair embeddings.

11. The method of claim 9, wherein:

the auxiliary folding prediction comprise structure parameters that specify a distance map that characterizes, for each pair of amino acids in the protein, a respective estimated distance between the pair of amino acids in the structure of the protein; and generating the transformed structure prediction comprises:

generating, from the distance map specified by the structure parameters, a transformed distance map that has a same dimensionality as the initial pair embeddings.

12. The method of claim 1, further comprising:

after the training, obtaining a new network input characterizing a new protein; and processing the new network input using the trained structure prediction neural network to generate a new main structure prediction that defines a predicted structure of the new protein.

13. A system comprising:

one or more computers; and one or more storage devices communicatively coupled to the one or more computers, wherein the one or more storage devices store instructions that, when executed by the one or more computers, cause the one or more computers to perform operations for training a structure prediction neural network, wherein the structure prediction neural network comprises (i) an embedding neural network having a plurality of embedding parameters and that is configured to receive a network input characterizing a protein and to process the network input in accordance with the embedding parameters to generate an embedding output for the network input and (ii) a main folding neural network having a plurality of main folding parameters and that is configured to receive the embedding output and to process the embedding output in accordance with the main folding parameters to generate a main structure prediction that defines a predicted structure of the protein, the operations comprising:

obtaining a training network input characterizing a training protein and data specifying a target protein structure for the training protein;

processing the training network input using the embedding neural network and in accordance with current values of the embedding parameters to generate a training embedding output for the training network input;

processing the training embedding output using the main folding neural network and in accordance with current values of the main folding parameters to generate a main structure prediction that defines a main predicted structure of the training protein;

for each auxiliary folding neural network in a set of one or more auxiliary folding neural networks that each have a respective plurality of auxiliary folding parameters, processing at least a corresponding intermediate output of the embedding neural network using the auxiliary folding neural network and in accordance with current values of the respective auxiliary folding parameters of the auxiliary folding neural network to generate an auxiliary structure prediction that defines an auxiliary predicted structure of the training protein;

determining a gradient of an objective function that includes:

a main structure loss term that characterizes a similarity between: (i) the main predicted structure defined by the main structure prediction, and (ii) the target protein structure for the training protein; and a respective auxiliary structure loss term for each of the auxiliary folding neural networks that characterizes a similarity between: (i) the auxiliary predicted structure defined by the auxiliary structure prediction generated by the auxiliary structure prediction neural network, and (ii) the target protein structure for the training protein; and updating the current values of the embedding network parameters, the main folding, parameters, and the respective auxiliary folding parameters of the one or more auxiliary folding neural networks based on the gradient.

14. One or more non-transitory computer storage media storing instructions that when executed by one or more computers cause the one or more computers to perform operations for training a structure prediction neural network, wherein the structure prediction neural network comprises (i) an embedding neural network having a plurality of embedding parameters and that is configured to receive a network input characterizing a protein and to process the network input in accordance with the embedding parameters to generate an embedding output for the network input and (ii) a main folding neural network having a plurality of main folding parameters and that is configured to receive the embedding output and to process the embedding output in accordance with the main folding parameters to generate a main structure prediction that defines a predicted structure of the protein, the operations comprising:

obtaining a training network input characterizing a training protein and data specifying a target protein structure for the training protein;

processing the training network input using the embedding neural network and in accordance with current values of the embedding parameters to generate a training embedding output for the training network input;

processing the training embedding output using the main folding neural network and in accordance with current values of the main folding parameters to generate a main structure prediction that defines a main predicted structure of the training protein;

for each auxiliary folding neural network in a set of one or more auxiliary folding neural networks that each have a respective plurality of auxiliary folding parameters, processing at least a corresponding intermediate output of the embedding neural network using the auxiliary folding neural network and in accordance with current values of the respective auxiliary folding parameters of the auxiliary folding neural network to generate an auxiliary structure prediction that defines an auxiliary predicted structure of the training protein;

determining a gradient of an objective function that includes:

a main structure loss term that characterizes a similarity between: (i) the main predicted structure defined by the main structure prediction, and (ii) the target protein structure for the training protein; and a respective auxiliary structure loss term for each of the auxiliary folding neural networks that characterizes a similarity between: (i) the auxiliary predicted structure defined by the auxiliary structure prediction generated by the auxiliary structure prediction neural network, and (ii) the target protein structure for the training protein; and updating the current values of the embedding network parameters, the main folding parameters, and the respective auxiliary folding parameters of the one or more auxiliary folding neural networks based on the gradient.

15. The non-transitory computer storage media of claim 14, wherein each auxiliary folding neural network has a same neural network architecture as the main folding neural network.

16. The non-transitory computer storage media of claim 15, wherein the set of one or more auxiliary folding neural networks comprises a plurality of auxiliary folding neural networks and wherein the objective function constrains the auxiliary folding neural networks to share parameter values.

17. The non-transitory computer storage media of claim 15, wherein the objective function constrains the auxiliary folding neural networks and the main folding neural network to share parameter values.

18. The non-transitory computer storage media of claim 14, wherein:

the network input comprises a respective initial pair embedding for each pair of amino acids in the protein, the embedding neural network comprises a sequence of update blocks, wherein each update block performs operations comprising:

receiving a block input comprising a respective current pair embedding for each pair of amino acids in the protein; and updating the respective current pair embeddings for each pair of amino acids in the protein to generate a respective updated pair embedding for each pair of amino acids in the protein, and the embedding output comprises at least the updated pair embeddings generated by a last update block in the sequence.

19. The non-transitory computer storage media of claim 18, wherein each auxiliary folding neural network corresponds to a different one of the update blocks in the sequence that is not the last update block in the sequence, and wherein each auxiliary folding neural network is configured to receive as input at least the updated pair embeddings generated by the corresponding update block.

20. The non-transitory computer storage media of claim 19, wherein:

the network input further comprises an initial multiple sequence alignment (MSA) embedding that represents a respective multiple sequence alignment corresponding to each chain in the protein, the block input to each of the update blocks further comprises a current MSA embedding; and the operations performed by each update block further comprise:

updating the current MSA embedding to generate an updated MSA embedding.

* * * * *